(12) United States Patent
High et al.

(10) Patent No.: US 7,211,558 B2
(45) Date of Patent: May 1, 2007

(54) COMPOSITIONS AND METHODS FOR THE TREATMENT OF HEMOPHILIA A

(75) Inventors: Katherine A. High, Merion, PA (US); Rodney M. Camire, Voorhees, NJ (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 86 days.

(21) Appl. No.: 10/445,235

(22) Filed: May 22, 2003

(65) Prior Publication Data

US 2004/0005670 A1  Jan. 8, 2004

Related U.S. Application Data

(60) Provisional application No. 60/382,486, filed on May 22, 2002.

(51) Int. Cl.
| | |
|---|---|
| *A61K 38/00* | (2006.01) |
| *A61K 35/14* | (2006.01) |
| *A61K 35/16* | (2006.01) |
| *C12K 14/00* | (2006.01) |
| *C12N 15/63* | (2006.01) |
| *C07H 21/02* | (2006.01) |
| *C07H 21/04* | (2006.01) |
| *A61K 48/00* | (2006.01) |

(52) U.S. Cl. .................. 514/2; 514/44; 435/320.1; 530/350; 530/383; 536/23.1

(58) Field of Classification Search ............... 536/23.1; 514/2, 44; 435/320.1; 530/350, 383
See application file for complete search history.

(56) References Cited

U.S. PATENT DOCUMENTS 5,171,844 A * 12/1992 van Ooyen et al. ......... 530/383

5,460,950 A * 10/1995 Barr et al. .................. 435/69.1

OTHER PUBLICATIONS

Nesheim et al. The Effect of Plasma von Willebrand Factor on the Binding of Human Factor VIII to Thrombin-activated Human Platelets. (1991) J. Biol. Chem. vol. 266, No. 27, pp. 17815-17820.*
Antonarakis et al., Molecular Genetics of Hemophilia A in Man (Factor VIII Deficiency), Mol. Biol. Med. (1987) 4, pp. 81-94.
Berntorp, Second Generation, B-Domain Deleted Recombinant Factor VIII, Thrombosis and Hemostasis, (1997) 78(1), pp. 256-260.
Brinkhous et al., Purified human factor VIII procoagulant protein: Comparative hemostatic response after infusions into hemophilic and Von Willebrand disease dogs, PNAS (1985) 82, pp. 8752-8756.
Lind et al., Novel forms of B-domain-deleted recombinant factor VIII molecules. Construction and biochemical characterization, Eur. J. Biochem. (1995) 232, 19-27.
Lusher et al., Recombinant Factor VIII for the Treatment of Previously Untreated Patients with Hemophilia A, The New England Journal of Medicine (1993), 328(7), pp. 453-459.
Pittman et al., A2 Domain of Human Recombinant-Derived Factor VIII is Required for Procoagulant Activity but not for Thrombin Cleavage, Blood (1992), 79(2), pp. 389-397.
Sandberg et al., Structural and Functional Characterization of B-Domain Deleted Recombinant Factor VIII, Seminars in Hematology, (2001) 38(2), pp. 4-12.
Toole et al., Molecular cloning of a cDNA encoding human anti-haemophillic factor, Nature (1984) 312(22), pp. 342-347.
Vehar et al., Structure of human factor VIII, Nature (1984) 312(22), pp. 337-342.
Wood et al., Expression of active human factor VIII from recombinant DNA clones, Nature (1984) 312(22), pp. 330-337.

* cited by examiner

*Primary Examiner*—Nashaat T. Nashed
*Assistant Examiner*—Holly Schnizer
(74) *Attorney, Agent, or Firm*—Dann Dorfman Herrell & Skillman; Kathleen D. Rigaut; Robert C. Netter, Jr.

(57) ABSTRACT

Improved materials and methods for the treatment of Hemophilia A are provided.

9 Claims, 7 Drawing Sheets

Stable Expression of rFVIII Constructs:

| Construct | Test-1 | Test-2 |
|---|---|---|
| rFVIII-SQ | Clotting: 3.06 U/mL<br>ELISA: 703 ng/mL<br>4361 IU/mg | Clotting: 2.93 U/mL<br>ELISA: 623 ng/mL<br>4710 IU/mg |
| rFVIII-RKR | Clotting: 5.1 U/mL<br>ELISA: 145 ng/mL<br>35039 IU/mg | Clotting: 3.8 U/mL<br>ELISA: 122 ng/mL<br>31149 IU/mg |
| Ratio of rFVIII-RKR/rFVIII-SQ | 8.03 | 6.61 |

Figure 6

ID NO: 1). Within SEQ ID NO: 1, nucleic acids 208–7206

SEQUENCE LISTING

<160> NUMBER OF SEQ ID NOS: 9

<210> SEQ ID NO 1
<211> LENGTH: 9009
<212> TYPE: DNA
<213> ORGANISM: homo sapiens

<400> SEQUENCE: 1

-continued

| | |
|---|---|
| cagtgggtaa gttccttaaa tgctctgcaa agaaattggg acttttcatt aaatcagaaa | 60 |
| ttttactttt ttcccctcct gggagctaaa gatattttag agaagaatta accttttgct | 120 |
| tctccagttg aacatttgta gcaataagtc atgcaaatag agctctccac ctgcttcttt | 180 |
| ctgtgccttt tgcgattctg ctttagtgcc accagaagat actacctggg tgcagtggaa | 240 |
| ctgtcatggg actatatgca aagtgatctc ggtgagctgc ctgtggacgc aagatttcct | 300 |
| cctagagtgc caaaatcttt tccattcaac acctcagtcg tgtacaaaaa gactctgttt | 360 |
| gtagaattca cggttcacct tttcaacatc gctaagccaa ggccaccctg gatgggtctg | 420 |
| ctaggtccta ccatccaggc tgaggtttat gatacagtgg tcattacact aagaacatg | 480 |
| gcttcccatc ctgtcagtct tcatgctgtt ggtgtatcct actggaaagc ttctgaggga | 540 |
| gctgaatatg atgatcagac cagtcaaagg gagaaagaag atgataaagt cttccctggt | 600 |
| ggaagccata catatgtctg gcaggtcctg aaagagaatg gtccaatggc ctctgaccca | 660 |
| ctgtgcctta cctactcata tctttctcat gtggacctgg taaaagactt gaattcaggc | 720 |
| ctcattggag ccctactagt atgtagagaa gggagtctgg ccaaggaaaa gacacagacc | 780 |
| ttgcacaaat ttatactact ttttgctgta tttgatgaag ggaaaagttg gcactcagaa | 840 |
| acaaagaact ccttgatgca ggatagggat gctgcatctg ctcgggcctg gcctaaaatg | 900 |
| cacacagtca atggttatgt aaacaggtct ctgccaggtc tgattggatg ccacaggaaa | 960 |
| tcagtctatt ggcatgtgat tggaatgggc accactcctg aagtgcactc aatattcctc | 1020 |
| gaaggtcaca catttcttgt gaggaaccat cgccaggcgt ccttggaaat ctcgccaata | 1080 |
| actttcctta ctgctcaaac actcttgatg gaccttggac agtttctact gttttgtcat | 1140 |
| atctcttccc accaacatga tggcatggaa gcttatgtca aagtagacag ctgtccagag | 1200 |
| gaacccaac tacgaatgaa aaataatgaa gaagcggaag actatgatga tgatcttact | 1260 |
| gattctgaaa tggatgtggt caggtttgat gatgacaact ctccttcctt tatccaaatt | 1320 |
| cgctcagttg ccaagaagca tcctaaaact tgggtacatt acattgctgc tgaagaggag | 1380 |
| gactgggact atgctccctt agtcctcgcc cccgatgaca gaagttataa aagtcaatat | 1440 |
| ttgaacaatg gccctcagcg gattggtagg aagtacaaaa aagtccgatt tatggcatac | 1500 |
| acagatgaaa cctttaagac tcgtgaagct attcagcatg aatcaggaat cttgggacct | 1560 |
| ttactttatg gggaagttgg agacacactg ttgattatat ttaagaatca agcaagcaga | 1620 |
| ccatataaca tctaccctca cggaatcact gatgtccgtc ctttgtattc aaggagatta | 1680 |
| ccaaaaggtg taaacatttt gaaggatttt ccaattctgc caggagaaat attcaaatat | 1740 |
| aaatggacag tgactgtaga agatgggcca actaaatcag atcctcggtg cctgacccgc | 1800 |
| tattactcta gtttcgttaa tatggagaga gatctagctt caggactcat ggccctctc | 1860 |
| ctcatctgct acaaagaatc tgtagatcaa agaggaaacc agataatgtc agacaagagg | 1920 |
| aatgtcatcc tgttttctgt atttgatgag aaccgaagct ggtacctcac agagaatata | 1980 |
| caacgctttc tccccaatcc agctggagtg cagcttgagg atccagagtt ccaagcctcc | 2040 |
| aacatcatgc acagcatcaa tggctatgtt tttgatagtt tgcagttgtc agtttgtttg | 2100 |
| catgaggtgg catactggta cattctaagc attggagcac agactgactt cctttctgtc | 2160 |
| ttcttctctg gatatacctt caaacacaaa atggtctatg aagacacact caccctattc | 2220 |
| ccattctcag agaaactgt cttcatgtcg atggaaaacc aggtctatg gattctgggg | 2280 |
| tgccacaact cagactttcg gaacagaggc atgaccgcct tactgaaggt ttctagttgt | 2340 |
| gacaagaaca ctggtgatta ttacgaggac agttatgaag atatttcagc atacttgctg | 2400 |

-continued

```
agtaaaaaca atgccattga accaagaagc ttctcccaga attcaagaca ccctagcact   2460
aggcaaaagc aatttaatgc caccacaatt ccagaaaatg acatagagaa gactgaccct   2520
tggtttgcac acagaacacc tatgcctaaa atacaaaatg tctcctctag tgatttgttg   2580
atgctcttgc gacagagtcc tactccacat gggctatcct tatctgatct ccaagaagcc   2640
aaatatgaga cttttctga tgatccatca cctggagcaa tagacagtaa taacagcctg   2700
tctgaaatga cacacttcag gccacagctc catcacagtg gggacatggt atttacccct   2760
gagtcaggcc tccaattaag attaaatgag aaactgggga caactgcagc aacagagttg   2820
aagaaacttg atttcaaagt ttctagtaca tcaaataatc tgatttcaac aattccatca   2880
gacaatttgg cagcaggtac tgataataca agttccttag acccccaag tatgccagtt    2940 cattatgata gtcaattaga taccactcta tttggcaaaa agtcatctcc ccttactgag   3000
tctggtggac ctctgagctt gagtgaagaa aataatgatt caaagttgtt agaatcaggt   3060
ttaatgaata gccaagaaag ttcatgggga aaaaatgtat cgtcaacaga gagtggtagg   3120
ttatttaaag ggaaaagagc tcatggacct gctttgttga ctaaagataa tgccttattc   3180
aaagttagca tctctttgtt aaagacaaac aaaacttcca ataattcagc aactaataga   3240
aagactcaca ttgatggccc atcattatta attgagaata gtccatcagt ctggcaaaat   3300
atattagaaa gtgacactga gtttaaaaaa gtgacacctt tgattcatga cagaatgctt   3360
atggacaaaa atgctacagc tttgaggcta aatcatatgt caaataaaac tacttcatca   3420
aaaaacatgg aaatggtcca acagaaaaaa gagggcccca ttccaccaga tgcacaaaat   3480
ccagatatgt cgttctttaa gatgctattc ttgccagaat cagcaaggtg gatacaaagg   3540
actcatggaa agaactctct gaactctggg caaggcccca gtccaaagca attagtatcc   3600
ttaggaccag aaaaatctgt ggaaggtcag aatttcttgt ctgagaaaaa caaagtggta   3660
gtaggaaagg gtgaatttac aaaggacgta ggactcaaag agatggtttt tccaagcagc   3720
agaaacctat ttcttactaa cttggataat ttacatgaaa ataatacaca caatcaagaa   3780
aaaaaaattc aggaagaaat agaaagaag gaaacattaa tccaagagaa tgtagttttg    3840
cctcagatac atacagtgac tggcactaag aatttcatga agaacctttt cttactgagc   3900
actaggcaaa atgtagaagg ttcatatgag ggggcatatg ctccagtact tcaagatttt   3960
aggtcattaa atgattcaac aaatagaaca agaaacaca cagctcattt ctcaaaaaaa    4020
ggggaggaag aaaacttgga aggcttggga aatcaaacca agcaaattgt agagaaatat   4080
gcatgcacca caaggatatc tcctaataca agccagcaga attttgtcac gcaacgtagt   4140
aagagagctt tgaaacaatt cagactccca ctagaagaaa cagaacttga aaaaggata    4200 attgtggatg acacctcaac ccagtggtcc aaaaacatga acatttgac cccgagcacc    4260 ctcacacaga tagactacaa tgagaaggag aaaggggcca ttactcagtc tcccttatca   4320
gattgcctta cgaggagtca tagcatccct caagcaaata gatctccatt acccattgca   4380
aaggtatcat catttccatc tattagacct atatatctga ccagggtcct attccaagac   4440
aactcttctc atcttccagc agcatcttat agaaagaaag attctggggt ccaagaaagc   4500
agtcatttct tacaaggagc caaaaaaat aaccttctct tagccattct aaccttggag    4560
atgactggtg atcaaagaga ggttggctcc ctggggacaa gtgccacaaa ttcagtcaca   4620
tacaagaaag ttgagaacac tgttctcccg aaaccagact tgcccaaaac atctggcaaa   4680
gttgaattgc ttccaaaagt tcacatttat cagaaggacc tattccctac ggaaactagc   4740
```

-continued

```
aatgggtctc ctggccatct ggatctcgtg gaagggagcc ttcttcaggg aacagaggga    4800
gcgattaagt ggaatgaagc aaacagacct ggaaaagttc cctttctgag agtagcaaca    4860
gaaagctctg caaagactcc ctccaagcta ttggatcctc ttgcttggga taaccactat    4920
ggtactcaga taccaaaaga agagtggaaa tcccaagaga agtcaccaga aaaaacagct    4980
tttaagaaaa aggataccat tttgtccctg aacgcttgtg aaagcaatca tgcaatagca    5040
gcaataaatg agggacaaaa taagcccgaa atagaagtca cctgggcaaa gcaaggtagg    5100
actgaaaggc tgtgctctca aaacccacca gtcttgaaac gccatcaacg ggaaataact    5160
cgtactactc ttcagtcaga tcaagaggaa attgactatg atgataccat atcagttgaa    5220
atgaagaagg aagattttga catttatgat gaggatgaaa atcagagccc ccgcagcttt    5280
caaaagaaaa cacgacacta ttttattgct gcagtggaga ggctctggga ttatgggatg    5340
agtagctccc cacatgttct aagaaacagg gctcagagtg gcagtgtccc tcagttcaag    5400
aaagttgttt tccaggaatt tactgatggc tcctttactc agcccttata ccgtggagaa    5460
ctaaatgaac atttgggact cctggggcca tatataagag cagaagttga agataatatc    5520
atggtaactt tcagaaatca ggcctctcgt ccctattcct tctattctag ccttatttct    5580
tatgaggaag atcagaggca aggagcagaa cctagaaaaa actttgtcaa gcctaatgaa    5640
accaaaactt acttttggaa agtgcaacat catatggcac ccactaaaga tgagtttgac    5700
tgcaaagcct gggcttattt ctctgatgtt gacctggaaa agatgtgcac ctcaggcctg    5760
attgaccccc ttctggtctg ccacactaac acactgaacc ctgctcatgg gagacaagtg    5820
acagtacagg aatttgctct gttttttcacc atctttgatg agaccaaaag ctggtacttc    5880
actgaaaata tggaaagaaa ctgcagggct ccctgcaata tccagatgga agatcccact    5940
tttaaagaga attatcgctt ccatgcaatc aatggctaca taatggatac actacctggc    6000
ttagtaatgg ctcaggatca aaggattcga tggtatctgc tcagcatggg cagcaatgaa    6060
aacatccatt ctattcattt cagtggacat gtgttcactg tacgaaaaaa agaggagtat    6120
aaaatggcac tgtacaatct ctatccaggt gtttttgaga cagtggaaat gttaccatcc    6180
aaagctggaa tttggcgggt ggaatgcctt attggcgagc atctacatgc tgggatgagc    6240 acacttttc tggtgtacag caataagtgt cagactcccc tgggaatggc ttctggacac    6300
attagagatt ttcagattac agcttcagga caatatggac agtgggcccc aaagctggcc    6360
agacttcatt attccggatc aatcaatgcc tggagcacca aggagccctt ttcttggatc    6420
aaggtggatc tgttggcacc aatgattatt cacggcatca agacccaggg tgcccgtcag    6480
aagttctcca gcctctacat ctctcagttt atcatcatgt atagtcttga tgggaagaag    6540
tggcagactt atcgaggaaa ttccactgga accttaatgg tcttctttgg caatgtggat    6600
tcatctggga taaaacacaa tattttaac cctccaatta ttgctcgata catccgtttg    6660
cacccaactc attatagcat tcgcagcact cttcgcatgg agttgatggg ctgtgattta    6720
aatagttgca gcatgccatt gggaatggag agtaaagcaa tatcagatgc acagattact    6780
gcttcatcct actttaccaa tatgtttgcc acctggtctc cttcaaaagc tcgacttcac    6840
ctccaaggga ggagtaatgc ctggagacct caggtgaata tccaaaagga gtggctgcaa    6900
gtggacttcc agaagacaat gaaagtcaca ggagtaacta ctcagggagt aaaatctctg    6960
cttaccagca tgtatgtgaa ggagttcctc atctccagca gtcaagatgg ccatcagtgg    7020
actctctttt ttcagaatgg caaagtaaag gttttcagg gaaatcaaga ctccttcaca    7080
cctgtggtga actctctaga cccaccgtta ctgactcgct accttcgaat tcaccccag    7140
```

```
agttgggtgc accagattgc cctgaggatg gaggttctgg gctgcgaggc acaggacctc    7200
tactgagggt ggccactgca gcacctgcca ctgccgtcac ctctccctcc tcagctccag    7260
ggcagtgtcc ctccctggct tgccttctac ctttgtgcta atcctagca gacactgcct     7320 tgaagcctcc tgaattaact atcatcagtc ctgcatttct ttggtggggg gccaggaggg    7380
tgcatccaat ttaacttaac tcttacctat tttctgcagc tgctcccaga ttactccttc    7440
cttccaatat aactaggcaa aagaagtga ggagaaacct gcatgaaagc attcttccct     7500
gaaaagttag gcctctcaga gtcaccactt cctctgttgt agaaaaacta tgtgatgaaa    7560 cttgaaaaa gatatttatg atgttaacat ttcaggttaa gcctcatacg tttaaaataa     7620
aactctcagt tgtttattat cctgatcaag catggaacaa agcatgtttc aggatcagat    7680
caatacaatc ttggagtcaa aaggcaaatc atttggacaa tctgcaaaat ggagagaata   7740
caataactac tacagtaaag tctgtttctg cttccttaca catagatata attatgttat    7800
ttagtcatta tgagggcac attcttatct ccaaaactag cattcttaaa ctgagaatta    7860
tagatggggt tcaagaatcc ctaagtcccc tgaaattata taaggcattc tgtataaatg    7920
caaatgtgca tttttctgac gagtgtccat agatataaag ccattggtct taattctgac    7980
caataaaaaa ataagtcagg aggatgcaat tgttgaaagc tttgaaataa aataacatgt    8040
cttcttgaaa tttgtgatgg ccaagaaaga aaatgatgat gacattaggc ttctaaagga    8100
catacattta atatttctgt ggaaatatga ggaaaatcca tggttatctg agataggaga    8160 tacaaactt gtaattctaa taatgcactc agtttactct ctccctctac taatttcctg     8220
ctgaaaataa cacaacaaaa atgtaacagg ggaaattata taccgtgact gaaaactaga    8280
gtcctactta catagttgaa atatcaagga ggtcagaaga aaattggact ggtgaaaaca    8340
gaaaaaacac tccagtctgc catatcacca cacaatagga tcccccttct tgccctccac    8400
ccccataaga ttgtgaaggg tttactgctc cttccatctg cctgcacccc ttcactatga    8460
ctacacagaa ctctcctgat agtaaagggg gctggaggca aggataagtt atagagcagt    8520
tggaggaagc atccaaagac tgcaacccag ggcaaatgga aaacaggaga tcctaatatg    8580
aaagaaaaat ggatcccaat ctgagaaaag gcaaagaat ggctactttt ttctatgctg     8640
gagtattttc taataatcct gcttgaccct tatctgacct cttttggaaac tataacatag    8700 ctgtcacagt atagtcacaa tccacaaatg atgcaggtgc aaatggttta tagccctgtg   8760
aagttcttaa agtttagagg ctaacttaca gaaatgaata agttgttttg ttttatagcc    8820
cggtagagga gttaacccca aaggtgatat ggttttattt cctgttatgt ttaacttgat    8880
aatcttattt tggcattctt ttcccattga ctatatacat ctctatttct caaatgttca    8940
tggaactagc tcttttattt tcctgctggt ttcttcagta atgagttaaa taaaacattg    9000
acacataca                                                            9009
```

<210> SEQ ID NO 2
<211> LENGTH: 2332
<212> TYPE: PRT
<213> ORGANISM: homo sapiens

<400> SEQUENCE: 2

Ala Thr Arg Arg Tyr Tyr Leu Gly Ala Val Glu Leu Ser Trp Asp Tyr
 1               5                   10                  15

Met Gln Ser Asp Leu Gly Glu Leu Pro Val Asp Ala Arg Phe Pro Pro
                20                  25                  30

```
Arg Val Pro Lys Ser Phe Pro Phe Asn Thr Ser Val Val Tyr Lys Lys
            35                  40                  45

Thr Leu Phe Val Glu Phe Thr Val His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Ile Thr Leu Lys Asn Met Ala Ser His Pro Val
                85                  90                  95

Ser Leu His Ala Val Gly Val Ser Tyr Trp Lys Ala Ser Glu Gly Ala
                100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
        210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
            325                 330                 335

Met Lys Asn Asn Glu Glu Ala Glu Asp Tyr Asp Asp Leu Thr Asp
        340                 345                 350

Ser Glu Met Asp Val Val Arg Phe Asp Asp Asn Ser Pro Ser Phe
        355                 360                 365

Ile Gln Ile Arg Ser Val Ala Lys Lys His Pro Lys Thr Trp Val His
370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
```

-continued

```
            450                 455                 460
Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
                500                 505                 510

Trp Thr Val Thr Val Glu Asp Gly Pro Thr Lys Ser Asp Pro Arg Cys
                515                 520                 525

Leu Thr Arg Tyr Tyr Ser Ser Phe Val Asn Met Glu Arg Asp Leu Ala
530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
                580                 585                 590

Arg Phe Leu Pro Asn Pro Ala Gly Val Gln Leu Glu Asp Pro Glu Phe
                595                 600                 605

Gln Ala Ser Asn Ile Met His Ser Ile Asn Gly Tyr Val Phe Asp Ser
                610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
                660                 665                 670

Phe Ser Gly Glu Thr Val Phe Met Ser Met Glu Asn Pro Gly Leu Trp
                675                 680                 685

Ile Leu Gly Cys His Asn Ser Asp Phe Arg Asn Arg Gly Met Thr Ala
                690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Ser Arg His Pro Ser Thr Arg
                740                 745                 750

Gln Lys Gln Phe Asn Ala Thr Thr Ile Pro Glu Asn Asp Ile Glu Lys
                755                 760                 765

Thr Asp Pro Trp Phe Ala His Arg Thr Pro Met Pro Lys Ile Gln Asn
770                 775                 780

Val Ser Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
                805                 810                 815

Ser Asp Asp Pro Ser Pro Gly Ala Ile Asp Ser Asn Asn Ser Leu Ser
                820                 825                 830

Glu Met Thr His Phe Arg Pro Gln Leu His His Ser Gly Asp Met Val
                835                 840                 845

Phe Thr Pro Glu Ser Gly Leu Gln Leu Arg Leu Asn Glu Lys Leu Gly
                850                 855                 860

Thr Thr Ala Ala Thr Glu Leu Lys Lys Leu Asp Phe Lys Val Ser Ser
865                 870                 875                 880
```

-continued

```
Thr Ser Asn Asn Leu Ile Ser Thr Ile Pro Ser Asp Asn Leu Ala Ala
            885                 890                 895

Gly Thr Asp Asn Thr Ser Ser Leu Gly Pro Pro Ser Met Pro Val His
            900                 905                 910

Tyr Asp Ser Gln Leu Asp Thr Leu Phe Gly Lys Lys Ser Ser Pro
            915                 920                 925

Leu Thr Glu Ser Gly Gly Pro Leu Ser Leu Ser Glu Glu Asn Asn Asp
            930                 935                 940

Ser Lys Leu Leu Glu Ser Gly Leu Met Asn Ser Gln Glu Ser Ser Trp
945                 950                 955                 960

Gly Lys Asn Val Ser Ser Thr Glu Ser Gly Arg Leu Phe Lys Gly Lys
                965                 970                 975

Arg Ala His Gly Pro Ala Leu Leu Thr Lys Asp Asn Ala Leu Phe Lys
            980                 985                 990

Val Ser Ile Ser Leu Leu Lys Thr Asn Lys Thr Ser Asn Asn Ser Ala
            995                 1000                1005

Thr Asn Arg Lys Thr His Ile Asp Gly Pro Ser Leu Leu Ile Glu Asn
        1010                1015                1020

Ser Pro Ser Val Trp Gln Asn Ile Leu Glu Ser Asp Thr Glu Phe Lys
1025                1030                1035                1040

Lys Val Thr Pro Leu Ile His Asp Arg Met Leu Met Asp Lys Asn Ala
            1045                1050                1055

Thr Ala Leu Arg Leu Asn His Met Ser Asn Lys Thr Thr Ser Ser Lys
            1060                1065                1070

Asn Met Glu Met Val Gln Gln Lys Lys Glu Gly Pro Ile Pro Pro Asp
            1075                1080                1085

Ala Gln Asn Pro Asp Met Ser Phe Phe Lys Met Leu Phe Leu Pro Glu
            1090                1095                1100

Ser Ala Arg Trp Ile Gln Arg Thr His Gly Lys Asn Ser Leu Asn Ser
1105                1110                1115                1120

Gly Gln Gly Pro Ser Pro Lys Gln Leu Val Ser Leu Gly Pro Glu Lys
                1125                1130                1135

Ser Val Glu Gly Gln Asn Phe Leu Ser Glu Lys Asn Lys Val Val Val
            1140                1145                1150

Gly Lys Gly Glu Phe Thr Lys Asp Val Gly Leu Lys Glu Met Val Phe
            1155                1160                1165

Pro Ser Ser Arg Asn Leu Phe Leu Thr Asn Leu Asp Asn Leu His Glu
            1170                1175                1180

Asn Asn Thr His Asn Gln Glu Lys Lys Ile Gln Glu Glu Ile Glu Lys
1185                1190                1195                1200

Lys Glu Thr Leu Ile Gln Glu Asn Val Val Leu Pro Gln Ile His Thr
            1205                1210                1215

Val Thr Gly Thr Lys Asn Phe Met Lys Asn Leu Phe Leu Leu Ser Thr
            1220                1225                1230

Arg Gln Asn Val Glu Gly Ser Tyr Glu Gly Ala Tyr Ala Pro Val Leu
            1235                1240                1245

Gln Asp Phe Arg Ser Leu Asn Asp Ser Thr Asn Arg Thr Lys Lys His
            1250                1255                1260

Thr Ala His Phe Ser Lys Lys Gly Glu Glu Asn Leu Glu Gly Leu
1265                1270                1275                1280

Gly Asn Gln Thr Lys Gln Ile Val Glu Lys Tyr Ala Cys Thr Thr Arg
            1285                1290                1295
```

-continued

Ile Ser Pro Asn Thr Ser Gln Asn Phe Val Thr Gln Arg Ser Lys
            1300                1305                1310

Arg Ala Leu Lys Gln Phe Arg Leu Pro Leu Glu Glu Thr Glu Leu Glu
        1315                1320            1325

Lys Arg Ile Ile Val Asp Asp Thr Ser Thr Gln Trp Ser Lys Asn Met
            1330                1335            1340

Lys His Leu Thr Pro Ser Thr Leu Thr Gln Ile Asp Tyr Asn Glu Lys
1345            1350                1355                1360

Glu Lys Gly Ala Ile Thr Gln Ser Pro Leu Ser Asp Cys Leu Thr Arg
            1365                1370            1375

Ser His Ser Ile Pro Gln Ala Asn Arg Ser Pro Leu Pro Ile Ala Lys
            1380                1385            1390

Val Ser Ser Phe Pro Ser Ile Arg Pro Ile Tyr Leu Thr Arg Val Leu
        1395                1400            1405

Phe Gln Asp Asn Ser Ser His Leu Pro Ala Ala Ser Tyr Arg Lys Lys
        1410                1415            1420

Asp Ser Gly Val Gln Glu Ser Ser His Phe Leu Gln Gly Ala Lys Lys
1425                1430            1435            1440

Asn Asn Leu Ser Leu Ala Ile Leu Thr Leu Glu Met Thr Gly Asp Gln
            1445                1450            1455

Arg Glu Val Gly Ser Leu Gly Thr Ser Ala Thr Asn Ser Val Thr Tyr
            1460                1465            1470

Lys Lys Val Glu Asn Thr Val Leu Pro Lys Pro Asp Leu Pro Lys Thr
        1475                1480            1485

Ser Gly Lys Val Glu Leu Leu Pro Lys Val His Ile Tyr Gln Lys Asp
        1490                1495            1500

Leu Phe Pro Thr Glu Thr Ser Asn Gly Ser Pro Gly His Leu Asp Leu
1505            1510                1515            1520

Val Glu Gly Ser Leu Leu Gln Gly Thr Glu Gly Ala Ile Lys Trp Asn
            1525                1530            1535

Glu Ala Asn Arg Pro Gly Lys Val Pro Phe Leu Arg Val Ala Thr Glu
            1540                1545            1550

Ser Ser Ala Lys Thr Pro Ser Lys Leu Leu Asp Pro Leu Ala Trp Asp
        1555                1560            1565

Asn His Tyr Gly Thr Gln Ile Pro Lys Glu Glu Trp Lys Ser Gln Glu
        1570                1575            1580

Lys Ser Pro Glu Lys Thr Ala Phe Lys Lys Lys Asp Thr Ile Leu Ser
1585            1590                1595            1600

Leu Asn Ala Cys Glu Ser Asn His Ala Ile Ala Ala Ile Asn Glu Gly
            1605                1610            1615

Gln Asn Lys Pro Glu Ile Glu Val Thr Trp Ala Lys Gln Gly Arg Thr
            1620                1625            1630

Glu Arg Leu Cys Ser Gln Asn Pro Pro Val Leu Lys Arg His Gln Arg
        1635                1640            1645

Glu Ile Thr Arg Thr Thr Leu Gln Ser Asp Gln Glu Glu Ile Asp Tyr
        1650                1655            1660

Asp Asp Thr Ile Ser Val Glu Met Lys Lys Glu Asp Phe Asp Ile Tyr
1665            1670                1675            1680

Asp Glu Asp Glu Asn Gln Ser Pro Arg Ser Phe Gln Lys Lys Thr Arg
            1685                1690            1695

His Tyr Phe Ile Ala Ala Val Glu Arg Leu Trp Asp Tyr Gly Met Ser
            1700                1705            1710

Ser Ser Pro His Val Leu Arg Asn Arg Ala Gln Ser Gly Ser Val Pro

-continued

Gln Phe Lys Lys Val Val Phe Gln Glu Phe Thr Asp Gly Ser Phe Thr
1715            1720                1725
                1730                1735            1740

Gln Pro Leu Tyr Arg Gly Glu Leu Asn Glu His Leu Gly Leu Leu Gly
1745            1750                1755            1760

Pro Tyr Ile Arg Ala Glu Val Glu Asp Asn Ile Met Val Thr Phe Arg
                1765                1770            1775

Asn Gln Ala Ser Arg Pro Tyr Ser Phe Tyr Ser Ser Leu Ile Ser Tyr
                1780            1785                1790

Glu Glu Asp Gln Arg Gln Gly Ala Glu Pro Arg Lys Asn Phe Val Lys
                1795            1800            1805

Pro Asn Glu Thr Lys Thr Tyr Phe Trp Lys Val Gln His His Met Ala
1810            1815                1820

Pro Thr Lys Asp Glu Phe Asp Cys Lys Ala Trp Ala Tyr Phe Ser Asp
1825            1830            1835            1840

Val Asp Leu Glu Lys Asp Val His Ser Gly Leu Ile Gly Pro Leu Leu
                1845            1850                1855

Val Cys His Thr Asn Thr Leu Asn Pro Ala His Gly Arg Gln Val Thr
                1860            1865                1870

Val Gln Glu Phe Ala Leu Phe Phe Thr Ile Phe Asp Glu Thr Lys Ser
                1875            1880            1885

Trp Tyr Phe Thr Glu Asn Met Glu Arg Asn Cys Arg Ala Pro Cys Asn
                1890            1895                1900

Ile Gln Met Glu Asp Pro Thr Phe Lys Glu Asn Tyr Arg Phe His Ala
1905            1910                1915            1920

Ile Asn Gly Tyr Ile Met Asp Thr Leu Pro Gly Leu Val Met Ala Gln
                1925            1930            1935

Asp Gln Arg Ile Arg Trp Tyr Leu Leu Ser Met Gly Ser Asn Glu Asn
                1940            1945            1950

Ile His Ser Ile His Phe Ser Gly His Val Phe Thr Val Arg Lys Lys
                1955            1960            1965

Glu Glu Tyr Lys Met Ala Leu Tyr Asn Leu Tyr Pro Gly Val Phe Glu
                1970            1975            1980

Thr Val Glu Met Leu Pro Ser Lys Ala Gly Ile Trp Arg Val Glu Cys
1985            1990            1995            2000

Leu Ile Gly Glu His Leu His Ala Gly Met Ser Thr Leu Phe Leu Val
                2005            2010            2015

Tyr Ser Asn Lys Cys Gln Thr Pro Leu Gly Met Ala Ser Gly His Ile
                2020            2025            2030

Arg Asp Phe Gln Ile Thr Ala Ser Gly Gln Tyr Gly Gln Trp Ala Pro
                2035            2040            2045

Lys Leu Ala Arg Leu His Tyr Ser Gly Ser Ile Asn Ala Trp Ser Thr
                2050            2055            2060

Lys Glu Pro Phe Ser Trp Ile Lys Val Asp Leu Leu Ala Pro Met Ile
2065            2070            2075            2080

Ile His Gly Ile Lys Thr Gln Gly Ala Arg Gln Lys Phe Ser Ser Leu
                2085            2090            2095

Tyr Ile Ser Gln Phe Ile Ile Met Tyr Ser Leu Asp Gly Lys Lys Trp
                2100            2105            2110

Gln Thr Tyr Arg Gly Asn Ser Thr Gly Thr Leu Met Val Phe Phe Gly
                2115            2120            2125

Asn Val Asp Ser Ser Gly Ile Lys His Asn Ile Phe Asn Pro Pro Ile
                2130            2135            2140

```
Ile Ala Arg Tyr Ile Arg Leu His Pro Thr His Tyr Ser Ile Arg Ser
2145                2150                2155                2160

Thr Leu Arg Met Glu Leu Met Gly Cys Asp Leu Asn Ser Cys Ser Met
            2165                2170                2175

Pro Leu Gly Met Glu Ser Lys Ala Ile Ser Asp Ala Gln Ile Thr Ala
                2180                2185                2190

Ser Ser Tyr Phe Thr Asn Met Phe Ala Thr Trp Ser Pro Ser Lys Ala
        2195                2200                2205

Arg Leu His Leu Gln Gly Arg Ser Asn Ala Trp Arg Pro Gln Val Asn
    2210                2215                2220

Asn Pro Lys Glu Trp Leu Gln Val Asp Phe Gln Lys Thr Met Lys Val
2225                2230                2235                2240

Thr Gly Val Thr Thr Gln Gly Val Lys Ser Leu Leu Thr Ser Met Tyr
                2245                2250                2255

Val Lys Glu Phe Leu Ile Ser Ser Ser Gln Asp Gly His Gln Trp Thr
                2260                2265                2270

Leu Phe Phe Gln Asn Gly Lys Val Lys Val Phe Gln Gly Asn Gln Asp
        2275                2280                2285

Ser Phe Thr Pro Val Val Asn Ser Leu Asp Pro Pro Leu Leu Thr Arg
        2290                2295                2300

Tyr Leu Arg Ile His Pro Gln Ser Trp Val His Gln Ile Ala Leu Arg
2305                2310                2315                2320

Met Glu Val Leu Gly Cys Glu Ala Gln Asp Leu Tyr
                2325                2330

<210> SEQ ID NO 3
<211> LENGTH: 19
<212> TYPE: PRT
<213> ORGANISM: homo sapiens

<400> SEQUENCE: 3

Met Gln Ile Glu Leu Ser Thr Cys Phe Phe Leu Cys Leu Leu Arg Phe
1               5                   10                  15

Cys Phe Ser

<210> SEQ ID NO 4
<211> LENGTH: 4
<212> TYPE: PRT
<213> ORGANISM: Artificial Sequence
<220> FEATURE:
<223> OTHER INFORMATION: Synthetic peptide

<400> SEQUENCE: 4

Arg Arg Arg Arg
1

<210> SEQ ID NO 5
<211> LENGTH: 6
<212> TYPE: PRT
<213> ORGANISM: Artificial Sequence
<220> FEATURE:
<223> OTHER INFORMATION: Synthetic peptide

<400> SEQUENCE: 5

Arg Lys Arg Arg Lys Arg
1               5

<210> SEQ ID NO 6
<211> LENGTH: 24
```

```
<212> TYPE: DNA
<213> ORGANISM: Artificial Sequence
<220> FEATURE:
<223> OTHER INFORMATION: Primer

<400> SEQUENCE: 6
ccactttgcc tttctctcca cagg                                          24

<210> SEQ ID NO 7
<211> LENGTH: 34
<212> TYPE: DNA
<213> ORGANISM: Artificial Sequence
<220> FEATURE:
<223> OTHER INFORMATION: Primer

<400> SEQUENCE: 7
gctttctacg ctttcttctt ggttcaatgg catt                               34

<210> SEQ ID NO 8
<211> LENGTH: 36
<212> TYPE: DNA
<213> ORGANISM: Artificial Sequence
<220> FEATURE:
<223> OTHER INFORMATION: Primer

<400> SEQUENCE: 8
agaaagcgta gaaagcgcag ctttcaaaag aaaaca                             36

<210> SEQ ID NO 9
<211> LENGTH: 24
<212> TYPE: DNA
<213> ORGANISM: Artificial Sequence
<220> FEATURE:
<223> OTHER INFORMATION: Primer

<400> SEQUENCE: 9 ctctttttt cgtacggtga acac                                           24
```

COMPOSITIONS AND METHODS FOR THE TREATMENT OF HEMOPHILIA A

CROSS REFERENCE TO RELATED APPLICATIONS

This application claims priority under 35 U.S.C. §119(e) to U.S. Provisional Patent Application No. 60/382,486 filed on May 22, 2002, the entire disclosure of which is incorporated by reference herein.

GOVERNMENT RIGHTS

Pursuant to 35 U.S.C. §202(c), it is acknowledged that the U.S. Government has certain rights in the invention described herein, which was made in part with funds from the National Institutes of Health, Grant Numbers: HL48322 and T32HL07439.

FIELD OF THE INVENTION

This invention relates to the fields of medicine and gene therapy. More specifically, the invention provides materials and methods for the restoring factor VIII activity in patients in need thereof.

BACKGROUND OF THE INVENTION

Several publications and patent documents are referenced in this application in order to more fully describe the state of the art to which this invention pertains. Full citations for these references are found at the end of the specification. The disclosure of each of these publications is incorporated by reference herein.

Hemophilia is a genetic disease characterized by a blood clotting deficiency. In hemophilia A (classic hemophilia, Factor VIII deficiency), an X-chromosome-linked genetic defect disrupts the gene encoding Factor VIII, a plasma glycoprotein, which is a key component in the blood clotting cascade. The cDNA sequence encoding human Factor VIII is available at GenBank with Accession No. K01740 (SEQ ID NO: 1). Within SEQ ID NO: 1, nucleic acids 208–7206 encode the full-length wild-type FVIII polypeptide (2332 amino acids, SEQ ID NO: 2) and nucleic acids 151–207 encode a preceding 19-residue signal sequence peptide (SEQ ID NO: 3). Human Factor VIII may be synthesized as a single chain polypeptide, with a predicted molecular weight of 265 kDa. The Factor VIII protein (SEQ ID NO: 2) has six domains, designated from the amino to the carboxy terminus as A1-A2-B-A3-C1-C2 (Wood et al., Nature 312: 330 [1984]; Vehar et al., Nature 312:337 [1984]; and Toole et al., Nature 312:342 [1984]). Human Factor VIII is processed within the cell to yield a heterodimer primarily comprised of a heavy chain of 200 kDa containing the A1, A2, and B domains and an 80 kDa light chain containing the A3, C1, and C2 domains (Kaufman et al., J. Biol. Chem., 263:6352–6362 [1988]). Both the single chain polypeptide and the heterodimer circulate in the plasma as inactive precursors (Ganz et al., Eur. J. Biochem., 170:521–528 [1988]). Activation of Factor VIII in plasma is initiated by thrombin cleavage between the A2 and B domains, which releases the B domain and results in a heavy chain consisting of the A1 and A2 domains. The 980 amino acid B domain is deleted in the activated procoagulant form of the protein. Additionally, in the native protein, two polypeptide chains ("a" and "b"), flanking the B domain, are bound to a divalent calcium cation. Hemophilia may result from point mutations, deletions, or mutations resulting in a stop codon (See, Antonarakis et al., Mol. Biol. Med., 4:81 [1987]).

The disease is relatively rare, afflicting approximately one in 10,000 males. Hemophilia in females is extremely rare, although it may occur in female children of an affected father and carrier mother, as well as in females with X-chromosomal abnormalities (e.g., Turner syndrome, X mosaicism, etc.). The severity of each patient's disease is broadly characterized into three groups—"mild," "moderate," and "severe," depending on the severity of the patient's symptoms and circulating Factor VIII levels. While normal levels of Factor VIII range between 50 and 200 ng/mL plasma, mildly affected patients have 6–60% of this value, and moderately affected patients have 1–5% of this value. Severely affected hemophiliacs have less than 1% of normal Factor VIII levels.

While hemophiliacs clearly require clotting factor after surgery or severe trauma, on a daily basis, spontaneous internal bleeding is a greater concern. Hemophiliacs experience spontaneous hemorrhages from early infancy, as well as frequent spontaneous hemarthroses and other hemorrhages requiring clotting factor replacement.

Without effective treatment, chronic hemophilic arthropathy occurs by young adulthood. Severely affected patients are prone to serious hemorrhages that may dissect through tissue planes, ultimately resulting in death due to compromised vital organs.

Clearly a need exists for improved compositions and methods for the treatment of this genetic disorder.

SUMMARY OF THE INVENTION

In accordance with the present invention, variant Factor VIII (FVIII) molecules having higher specific activity than native molecules are provided.

In one aspect, nucleic acid molecules encoding variant FVIII polypeptides are provided. These nucleic acids can be used to advantage in methods of gene therapy for the treatment of Hemophilia A.

In another aspect of the invention, the variant polypeptides described in Table II are expressed in a recombinant system, isolated and purified. The variant FVIII molecules are then formulated into a pharmaceutical composition for administration to patients in need thereof.

In yet further aspect of the invention, methods are provided for the treatment of Hemophilia A using the variant FVIII molecules disclosed herein.

BRIEF DESCRIPTION OF THE DRAWINGS

FIG. 6 shows the results obtained following stable transfection of BHK cells with constructs encoding recombinant Factor VIII. The data show that the constructs of the present invention produce FVIII with greater activity than prior art recombinant constructs.

DETAILED DESCRIPTION OF THE INVENTION

Figure 1:
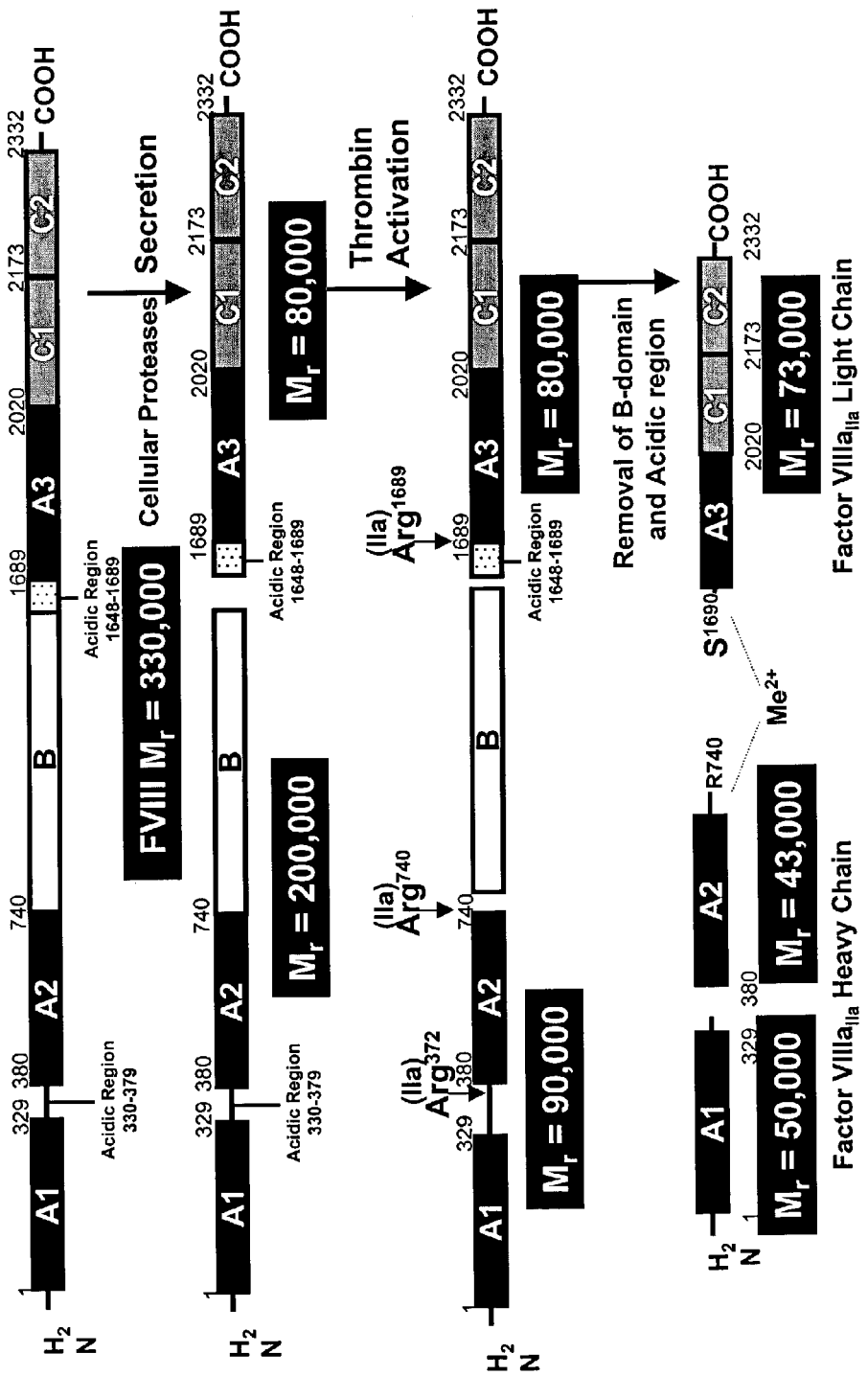
FIG. 1 is a schematic diagrams showing the proteolytic processing of human Factor VIII.

The invention described herein constitutes a novel form of the FVIII gene product for the treatment of Hemophilia A in a gene therapy or protein-based setting. An exemplary minigene of the invention consists of DNA sequences which encode for amino acids 1–740 of the heavy chain and 1690–2332 of the light chain (lacking the acidic region comprising amino acids 1648–1689 in the N-terminus of the light chain) which is interconnected by a linker DNA segment coding for a linker peptide which is recognized by the furin or furin-like enzymes (i.e. basic amino acids, RRRR (SEQ ID NO: 4) or RKRRKR (SEQ ID NO: 5) or any combination of basic residues which allows for efficient intracellular processing, such as when positions −1 and −4 relative to where cleavage occurs are arginines) Additionally, further deletion of the C-terminus of the heavy chain and the N-terminus of the light chain (with protease cleavage site in the middle, and combinations thereof) to further shorten the gene are also disclosed. This shortened form of the FVIII gene is more suitable for delivery via gene therapy than the full-length, native FVIII-encoding sequence and also creates a FVIII gene product with enhanced activity in the secreted form. While not wishing to be bound to any particular molecular theory, it appears that the protein is either activated more efficiently by thrombin or other activating protease to yield the active cofactor (FVIIIa) or, it may be secreted from the cell as a "partially" active pro-cofactor.

I. Definitions

The following definitions are provided to aid in understanding the subject matter regarded as the invention.

"Gene transfer" and "gene delivery" refer to methods or systems for reliably inserting a particular nucleic acid sequence into targeted cells.

As used herein, "Factor VIII (FVIII)" refers to a protein which functions as an essential co-factor in the activation of Factor X in the intrinsic blood coagulation system. FVIII minigene refers to a nucleic acid encoding modified FVIII proteins of the invention.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An isolated nucleic acid (either DNA or RNA) may further represent a molecule produced directly by biological or synthetic means and separated from other components present during its production.

"Natural allelic variants", "mutants" and "derivatives" of particular sequences of nucleic acids refer to nucleic acid sequences that are closely related to a particular sequence but which may possess, either naturally or by design, changes in sequence or structure. By closely related, it is meant that at least about 75%, but often, more than 90%, of the nucleotides of the sequence match over the defined length of the nucleic acid sequence referred to using a specific SEQ ID NO. Changes or differences in nucleotide sequence between closely related nucleic acid sequences may represent nucleotide changes in the sequence that arise during the course of normal replication or duplication in nature of the particular nucleic acid sequence. Other changes may be specifically designed and introduced into the sequence for specific purposes, such as to change an amino acid codon or sequence in a regulatory region of the nucleic acid. Such specific changes may be made in vitro using a variety of mutagenesis techniques or produced in a host organism placed under particular selection conditions that induce or select for the changes. Such sequence variants generated specifically may be referred to as "mutants" or "derivatives" of the original sequence.

The terms "percent similarity", "percent identity" and "percent homology" when referring to a particular sequence are used as set forth in the University of Wisconsin GCG software program.

A "fragment" or "portion" of the FVIII recombinant polypeptide means a stretch of amino acid residues of at least about five to seven contiguous amino acids, often at least about seven to nine contiguous amino acids, typically at least about nine to thirteen contiguous amino acids and, most preferably, at least about twenty to thirty or more contiguous amino acids.

A "derivative" of the FVIII recombinant polypeptide or a fragment thereof means a polypeptide modified by varying the amino acid sequence of the protein, e.g. by manipulation of the nucleic acid encoding the protein or by altering the protein itself. Such derivatives of the natural amino acid sequence may involve insertion, addition, deletion or substitution of one or more amino acids, and may or may not alter the essential activity of original the FVIII polypeptide.

As mentioned above, the FVIII recombinant polypeptide or protein of the invention includes any analogue, fragment, derivative or mutant which is derived from a FVIII recombinant polypeptide and which retains at least one property or other characteristic of the FVIII recombinant polypeptide. Different "variants" of the FVIII recombinant polypeptide may be generated. These variants may be alleles characterized by differences in the nucleotide sequences of the gene coding for the protein, or may involve different RNA processing or post-translational modifications. A skilled person can produce variants having single or multiple amino acid substitutions, deletions, additions or replacements. These variants may include inter alia: (a) variants in which one or more amino acids residues are substituted with conservative or non-conservative amino acids, (b) variants in which one or more amino acids are added to the FVIII recombinant polypeptide, (c) variants in which one or more amino acids include a substituent group, and (d) variants in which the FVIII recombinant polypeptide is fused with another peptide or polypeptide such as a fusion partner, a protein tag or other chemical moiety, that may confer useful properties to the FVIII recombinant polypeptide, such as, for example, an epitope for an antibody, a polyhistidine sequence, a biotin moiety and the like.

To the extent such allelic variations, analogues, fragments, derivatives, mutants, and modifications, including alternative nucleic acid processing forms and alternative post-translational modification forms result in derivatives of the FVIII recombinant polypeptide that retain any of the biological properties of the FVIII polypeptide, they are included within the scope of this invention.

The term "functional" as used herein implies that the nucleic or amino acid sequence is functional for the recited assay or purpose.

The phrase "consisting essentially of" when referring to a particular nucleotide or amino acid means a sequence having the properties of a given SEQ ID No:. For example, when used in reference to an amino acid sequence, the phrase includes the sequence per se and molecular modifications that would not affect the functional and novel characteristics of the sequence.

A "replicon" is any genetic element, for example, a plasmid, cosmid, bacmid, phage or virus, that is capable of replication largely under its own control. A replicon may be either RNA or DNA and may be single or double stranded.

A "vector" is a replicon, such as a plasmid, cosmid, bacmid, phage or virus, to which another genetic sequence or element (either DNA or RNA) may be attached so as to bring about the replication of the attached sequence or element. Exemplary vectors of the invention include without limitation, adenoviral-based vectors, adeno-associated viral vectors, retroviral vectors, and transposon-transposase vector systems (Cell 91:501–10, 1991; Nature Genetics 25:35–41, 2000).

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

The term "oligonucleotide," as used herein refers to primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15–25 or more nucleotides, although it may contain fewer nucleotides. The probes herein are selected to be "substantially" complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specfically.

The term "specifically hybridize" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield an primer extension product. The primer may vary in length depending on the particular conditions and requirement of the application. For example, in diagnostic applications, the oligonucleotide primer is typically 15–25 or more nucleotides in length. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product. Amino acid residues described herein are preferred to be in the "L" isomeric form. However, residues in the "D" isomeric form may be substituted for any L-amino acid residue, provided the desired properties of the polypeptide are retained.

All amino-acid residue sequences represented herein conform to the conventional left-to-right amino-terminus to carboxy-terminus orientation.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

The term "substantially pure" refers to a preparation comprising at least 50–60% by weight of a given material (e.g., nucleic acid, oligonucleotide, protein, etc.). More preferably, the preparation comprises at least 75% by weight, and most preferably 90–95% by weight of the given compound. Purity is measured by methods appropriate for the given compound (e.g. chromatographic methods, agarose or polyacrylamide gel electrophoresis, HPLC analysis, and the like).

"Mature protein" or "mature polypeptide" shall mean a polypeptide possessing the sequence of the polypeptide after any processing events that normally occur to the polypeptide during the course of its genesis, such as proteolytic processing from a polyprotein precursor. In designating the sequence or boundaries of a mature protein, the first amino of the mature protein sequence is designated as amino acid residue 1.

The term "tag," "tag sequence" or "protein tag" refers to a chemical moiety, either a nucleotide, oligonucleotide, polynucleotide or an amino acid, peptide or protein or other chemical, that when added to another sequence, provides additional utility or confers useful properties, particularly in the detection or isolation, to that sequence. Thus, for example, a homopolymer nucleic acid sequence or a nucleic acid sequence complementary to a capture oligonucleotide may be added to a primer or probe sequence to facilitate the subsequent isolation of an extension product or hybridized product. In the case of protein tags, histidine residues (e.g., 4 to 8 consecutive histidine residues) may be added to either the amino- or carboxy-terminus of a protein to facilitate protein isolation by chelating metal chromatography. Alternatively, amino acid sequences, peptides, proteins or fusion partners representing epitopes or binding determinants reactive with specific antibody molecules or other molecules (e.g., flag epitope, c-myc epitope, transmembrane epitope of the influenza A virus hemaglutinin protein, protein A, cellulose binding domain, calmodulin binding protein, maltose binding protein, chitin binding domain, glutathione S-transferase, and the like) may be added to proteins to facilitate protein isolation by procedures such as affinity or immunoaffinity chromatography. Chemical tag moieties include such molecules as biotin, which may be added to either nucleic acids or proteins and facilitates isolation or detection by interaction with avidin reagents, and the like. Numerous other tag moieties are known to, and can be envisioned by, the trained artisan, and are contemplated to be within the scope of this definition.

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radioimmunoassay, or by calorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, poly A addition signals, transcriptional termination signals and the like.

The terms "transform", "transfect", "transduce", shall refer to any method or means by which a nucleic acid is introduced into a cell or host organism and may be used interchangeably to convey the same meaning. Such methods include, but are not limited to, transfection, electroporation, microinjection, PEG-fusion and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. In other manners, the introduced nucleic acid may exist in the recipient cell or host organism only transiently.

A "clone" or "clonal cell population" is a population of cells derived from a single cell or common ancestor by mitosis.

A "cell line" is a clone of a primary cell or cell population that is capable of stable growth in vitro for many generations.

II. Preparation of FVIII-Encoding Nucleic Acid Molecules, FVIII Proteins, and Antibodies Thereto A. Nucleic Acid Molecules Nucleic acid molecules encoding the recombinant FVIII of the invention may be prepared by two general methods: (1) Synthesis from appropriate nucleotide triphosphates, or (2) recombinant cloning of nucleic acid sequences encoding modified FVIII. Both methods utilize protocols well known in the art.

The availability of nucleotide sequence information, such as cDNA having the sequence of SEQ ID NO: 1 or segments thereof, enables preparation of an isolated nucleic acid molecule of the invention by oligonucleotide synthesis. Synthetic oligonucleotides may be prepared by the phosphoramidite method employed in the Applied Biosystems 38A DNA Synthesizer or similar devices. The resultant construct may be purified according to methods known in the art, such as high performance liquid chromatography (HPLC). Long, double-stranded polynucleotides, such as a DNA molecule of the present invention, must be synthesized in stages, due to the size limitations inherent in current oligonucleotide synthetic methods. Thus, for example, a 2.4 kb double-stranded molecule may be synthesized as several smaller segments of appropriate complementarity. Complementary segments thus produced may be annealed such that each segment possesses appropriate cohesive termini for attachment of an adjacent segment. Adjacent segments may be ligated by annealing cohesive termini in the presence of DNA ligase to construct an entire 2.4 kb double-stranded molecule. A synthetic DNA molecule so constructed may then be cloned and amplified in an appropriate vector.

Nucleic acid sequences encoding FVIII may be isolated from appropriate biological sources using methods known in the art and then modified in accordance with the teachings in the present specification. In a preferred embodiment, a cDNA clone is isolated from a cDNA expression library of human origin.

FVIII-encoding nucleic acid molecules of the invention include cDNA, genomic DNA, RNA, and fragments thereof which may be single- or double-stranded. Thus, this invention provides oligonucleotides (sense or antisense strands of DNA or RNA) having sequences capable of hybridizing with at least one sequence of a nucleic acid molecule of the present invention, such as selected segments of the cDNA having SEQ ID NO: 1. Such oligonucleotides are useful as probes for detecting or isolating FVIII genes.

Nucleic acid according to the present invention may be used in methods of gene therapy, for instance in treatment of individuals with the aim of preventing or curing (wholly or partially) Hemophilia A. This too is discussed below.

B. Proteins

FVIII protein functions as a co-factor in the blood coagulation system. A full-length FVIII protein of the present invention may be prepared in a variety of ways, according to known methods. The protein may be purified from appropriate sources, e.g., transformed bacterial or animal cultured cells or tissues, by immunoaffinity purification.

The availability of nucleic acid molecules encoding FVIII enables production of the protein using in vitro expression methods known in the art. For example, a cDNA or gene may be cloned into an appropriate in vitro transcription vector, such as pSP64 or pSP65 for in vitro transcription, followed by cell-free translation in a suitable cell-free translation system, such as wheat germ or rabbit reticulocyte lysates. In vitro transcription and translation systems are commercially available, e.g., from Promega Biotech, Madison, Wis. or BRL, Rockville, Md.

Alternatively, according to a preferred embodiment, larger quantities of FVIII may be produced by expression in a suitable prokaryotic or eukaryotic system. For example, part or all of a DNA molecule, such as the cDNA having SEQ ID NO: 1 or segments thereof, may be inserted into a plasmid vector adapted for expression in a bacterial cell, such as *E. coli*. Such vectors comprise the regulatory elements necessary for expression of the DNA in the host cell (e.g. *E. coli*) positioned in such a manner as to permit expression of the DNA in the host cell. Such regulatory elements required for expression include promoter sequences, transcription initiation sequences and, optionally, enhancer sequences.

The FVIII produced by gene expression in a recombinant prokaryotic or eukaryotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein or nickel columns for isolation of recombinant proteins tagged with 6–8 histidine residues at their N-terminus or C-terminus. Alternative tags may comprise the FLAG epitope or the hemagglutinin epitope. Such methods are commonly used by skilled practitioners.

As discussed above, a convenient way of producing a polypeptide according to the present invention is to express nucleic acid encoding it, by use of the nucleic acid in an expression system. The use of expression systems has reached an advanced degree of sophistication today.

Accordingly, the present invention also encompasses a method of making a polypeptide (as disclosed), the method including expression from nucleic acid encoding the polypeptide (generally nucleic acid according to the invention). This may conveniently be achieved by growing a host cell in culture, containing such a vector, under appropriate conditions which cause or allow production of the polypeptide. Polypeptides may also be produced in in vitro systems, such as reticulocyte lysate.

Polypeptides which are amino acid sequence variants, alleles, derivatives or mutants are also provided by the present invention. A polypeptide which is a variant, allele, derivative, or mutant may have an amino acid sequence that differs from that given in SEQ ID NO: 2 by one or more of addition, substitution, deletion and insertion of one or more amino acids. Preferred such polypeptides have FVIII function.

A polypeptide which is an amino acid sequence variant, allele, derivative or mutant of the amino acid sequence shown in SEQ ID NO: 2 may comprise an amino acid sequence which shares greater than about 35% sequence identity with the sequence shown, greater than about 40%, greater than about 50%, greater than about 60%, greater than about 70%, greater than about 80%, greater than about 90% or greater than about 95%. Particular amino acid sequence variants may differ from that shown in SEQ ID NO: 2 by insertion, addition, substitution or deletion of 1 amino acid, 2, 3, 4, 5–10, 10–20, 20–30, 30–40, 40–50, 50–100, 100–150, or more than 150 amino acids.

A polypeptide according to the present invention may be used in screening for molecules which affect or modulate its activity or function. Such molecules may be useful in a therapeutic (possibly including prophylactic) context.

III. Uses of Recombinant FVIII-Encoding Nucleic Acids, and Modified FVIII Proteins The nucleic acids encoding the recombinant FVIII of the invention may be used in gene therapy protocols for the treatment of Hemophilia A. The improved construct encoding FVIII can be inserted into the appropriate gene therapy vector and administered to a patient to correct FVIII deficiency.

Vectors, such as viral vectors have been used in the prior art to introduce genes into a wide variety of different target cells. Typically the vectors are exposed to the target cells so that transformation can take place in a sufficient proportion of the cells to provide a useful therapeutic or prophylactic effect from the expression of the desired polypeptide (e.g., FVIII). The transfected nucleic acid may be permanently incorporated into the genome of each of the targeted cells, providing long lasting effect, or alternatively the treatment may have to be repeated periodically.

A variety of vectors, both viral vectors and plasmid vectors are known in the art, see U.S. Pat. No. 5,252,479 and WO 93/07282. In particular, a number of viruses have been used as gene transfer vectors, including papovaviruses, such as SV40, vaccinia virus, herpes viruses including HSV and EBV, and retroviruses. Many gene therapy protocols in the prior art have employed disabled murine retroviruses.

Several recently issued patents are directed to methods and compositions for performing gene therapy. See U.S. Pat. Nos. 6,168,916; 6,135,976; 5,965,541 and 6,129,705. Each of the foregoing patents is incorporated by reference herein.

In another aspect of the invention, the variant FVIII polypeptide may be administered to patients. Pharmaceutical compositions containing variant FVIII, alone or in combination with appropriate pharmaceutical stabilization compounds, delivery vehicles, and/or carrier vehicles, are prepared according to known methods, as described in Remington's Pharmaceutical Sciences by E. W. Martin.

In one preferred embodiment, the preferred carriers or delivery vehicles for intravenous infusion are physiological saline or phosphate buffered saline.

In another preferred embodiment, suitable stabilization compounds, delivery vehicles, and carrier vehicles include but are not limited to other human or animal proteins such as albumin.

Phospholipid vesicles or liposomal suspensions are also preferred as pharmaceutically acceptable carriers or delivery vehicles. These can be prepared according to methods known to those skilled in the art and can contain, for example, phosphatidylserine/phosphatidylcholine or other compositions of phospholipids or detergents that together impart a negative charge to the surface, since FVIII binds to negatively charged phospholipid membranes. Liposomes may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the variant FVIII is then introduced into the container. The container is then swirled by hand to free lipid material from the sides of the container and to disperse lipid aggregates, thereby forming the liposomal suspension.

The variant FVIII can be combined with other suitable stabilization compounds, delivery vehicles, and/or carrier vehicles, including vitamin K dependent clotting factors, tissue factor, and von Willebrand factor (vWf) or a fragment of vWf that contains the FVIII binding site, and polysaccharides such as sucrose.

IV. Therapeutics

As mentioned previously, the FVIII-encoding nucleic acids or polypeptides/proteins, of the invention can be formulated in pharmaceutical compositions. These compositions may comprise, in addition to one of the above substances, a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal routes.

Whether it is a polypeptide, or nucleic acid molecule, according to the present invention that is to be given to an individual, administration is preferably in a "prophylactically effective amount" or a "therapeutically effective amount" (as the case may be, although prophylaxis may be considered therapy), this being sufficient to show benefit to the individual.

The treatment dosage of variant FVIII composition that must be administered to a patient in need of such treatment will vary depending on the severity of the FVIII deficiency. Generally, dosage level is adjusted in frequency, duration, and units in keeping with the severity and duration of each patient's bleeding episode. Accordingly, the variant FVIII is included in the pharmaceutically acceptable carrier, delivery vehicle, or stabilizer in an amount sufficient to deliver to patient a therapeutically effective amount of the variant protein to stop bleeding, as measured by standard clotting assays.

FVIII is classically defined as the substance present in normal blood plasma that corrects the clotting defect in plasma derived from individuals with hemophilia A. The coagulant activity in vitro of purified and partially-purified forms of FVIII is used to calculate the dose of FVIII for infusions in human patients and is a reliable indicator of activity recovered from patient plasma and of correction of the in vivo bleeding defect. There are no reported discrepancies between standard assay of novel FVIII molecules in vitro and their behavior in the dog infusion model or in human patients, according to Lusher, J. M. et al. 328 New Engl. J. Med. 328:453459; Pittman, D. D. et al. (1992) Blood 79:389–397; and Brinkhous et al. (1985) Proc. Natl. Acad. Sci. 82:8752–8755.

Usually, the described plasma FVIII level to be achieved in the patient through administration of the variant FVIII is in the range of 30–100% of normal. In a preferred mode of administration of the variant FVIII, the composition is given intravenously at a preferred dosage in the range from about 5 to 50 units/kg body weight, more preferably in a range of 10–50 units/kg body weight, and most preferably at a dosage of 20–40 units/kg body weight; the interval frequency is in the range from about 8 to 24 hours (in severely affected hemophiliacs); and the duration of treatment in days is in the range from 1 to 10 days or until the bleeding episode is resolved. See, e.g., Roberts, H. R., and M. R. Jones, "Hemophilia and Related Conditions-congenital deficiencies of Prothrombin (Facor II, Factor V, an Factors VII to XII)," ch. 153, 1453–1474, 1460, in Hematology, Williams, W. J., et al., ed. (1990). As in treatment with human or porcine FVIII, the amount of variant FVIII infused is defined by the one-stage FVIII coagulation assay and, in selected instances, in vivo recovery is determined by measuring the FVIII in the patient's plasma after infusion. It is to be understood that for any particular subject, specific dosage regimens should be adjusted over time according to the individual need and the professional judgment of the person administering or supervising the administration of the compositions, and that the concentration ranges set forth herein are exemplary only and are not intended to limit the scope of practice of the claimed composition.

Treatment can take the form of a single intravenous administration of the composition or periodic or continuous administration over an extended period of time, as required. Alternatively, variant FVIII can be administered subcutaneously or orally with liposomes in one or several doses at varying intervals of time.

The following example is provided to illustrate certain embodiments of the invention. It is not intended to limit the invention in any way.

EXAMPLE I

Novel Minigene Encoding Improved Factor VIII

In accordance with the present invention, new recombinant Factor VIII minigenes are provided which stimulate production of Factor VIII in cells comprising the minigene with higher activity than prior art recombinant constructs.

Native FVIII is synthesized as a single chain polypeptide (2332 amino acids) preceded by a 19-residue signal sequence and has a molecular weight of $M_r$=330,000. The signal sequence is removed upon translocation of FVIII into the ER and the native FVIII is then cleaved in the B-domain in connection with its secretion. This results in the release of a heterodimer comprised of a $M_r$=200,000 heavy chain and a $M_r$=80,000 light chain, the association of which is metal-ion dependent. See FIG. 1.

Creation of the FVIII Minigenes:

The FVIII cDNA in the expression plasmid pSP64 was purchased from the ATCC. Following a Sal I restriction digest, the FVIII cDNA was subcloned into the mammalian expression plasmid, pED. To fuse the heavy chain to the light chain with a furin-like cleavage site in the middle, the following specific oligonucleotide primers were constructed for rFVIII-RKR$^2$ (a similar set of primers were used for rFVIII-R4): forward primer A, 5'-CCACTTTGC-CTTTCTCTCCACAGG-3', (SEQ ID NO: 6), which corresponds to a region in the pED plasmid which is just 5'-prime to the FVIII cDNA; reverse primer B, 5'-GCTTTC-TACGCTTTCTTCTTGGTTCAATGGCATT-3' (SEQ ID NO: 7), in which the first 15 bp correspond to a RKRRKR sequence (SEQ ID NO: 5) and the remaining bp correspond to FVIII gene sequence coding for residues 740–735 of FVIII polypeptide (SEQ ID NO: 2); forward primer C, 5'-AGAAAGCGTAGAAAGCG-CAGCTTTCAAAAGAAAACA-3' (SEQ ID NO: 8), in which the first 18 bp correspond to a RKRRKR sequence (SEQ ID NO: 5) and the remaining bp correspond to FVIII gene sequence coding for residues 1690–1695 of FVIII polypeptide (SEQ ID NO: 2); and reverse primer D, 5'-CTCTTTTTTTCGTACGGTGAACAC-3' (SEQ ID NO: 9), in which the underlined portion is a BsiWI restriction site and the 24 bp correspond to FVIII gene sequence coding for residues 1969–1962 of FVIII polypeptide (SEQ ID NO: 2). The DNA sequence encoding the heavy and light chains along with the furin cleavage sites were ligated together by the technique of splicing by overlap extension or "gene-SOEing" where primers B and C are the SOEing primers and primers A and D are the outside primers. The resulting DNA fragment was digested with SpeI and BsiWI, gel purified, and subcloned into pED-FVIII, cut with the same enzymes to generated PEDFVIII-RKR$^2$ (or pEDFVIII-R4). To confirm the presence of the desired construct and to ensure the absence of polymerase induced errors, DNA sequencing of the entire insert was performed. The plasmid was introduced into bacterial cells (DH5α strain of *E. coli*) for propagation and large amounts of the plasmid DNA was purified by standard techniques. The final constructs are shown schematically in FIG. 3. Thus for rFVIII-R4 and rFVIII-RKR$^2$, we have: 1) amino acids 1–740 of SEQ ID NO: 2; 2) protease cleavage site, i.e., RRRR (SEQ ID NO: 4) or RKRRKR (SEQ ID NO: 5); and 3) amino acids 1690–2332 of SEQ ID NO: 2.

Similarly, minigenes coding for recombinant FVIII variants FVIII(Δ721–1689) and FVIII(Δ731–1689) were constructed. Recombinant FVIII (Δ721–1689) and FVIII (Δ731–1689) comprises 1) amino acids 1–720 or 1–730 of SEQ ID NO: 2; 2) protease cleavage site, i.e., RKRRKR (SEQ ID NO: 5); and 3) amino acids 1690–2332 of SEQ ID NO: 2.

FVIII is activated by thrombin through specific proteolytic cleavages in both the heavy and light chains. In the heavy chain, one cleavage occurs at amino acid Arg$^{372}$ to generate separate A1 and A2 domains and another at Arg$^{740}$ at the junction between the A2 domain and the B-domain resulting in the release of the B-domain. In the light chain there is a cleavage at Arg$^{1689}$ in the acidic region at the amino-terminal of the A3 domain, whereby a new N-terminus is created. Cleavages at 372 and 1689 are necessary for full activation of FVIII. The 200+80 heterodimer is thus converted to a heterotrimer as shown in FIG. 1.

A problem in the packaging of the rFVIII cDNA or various B-domainless derivatives (i.e. rFVIII-SQ; ReFacto) in various AAV serotypes and other gene delivery vectors is the size of the insert, which when combined with required regulatory elements, often exceeds the packaging capacity of these vectors. Thus, development of rFVIII gene constructs with minimal lengths is a necessary step in successful gene transfer methods for the treatment of Hemophilia A.

Figure 2:
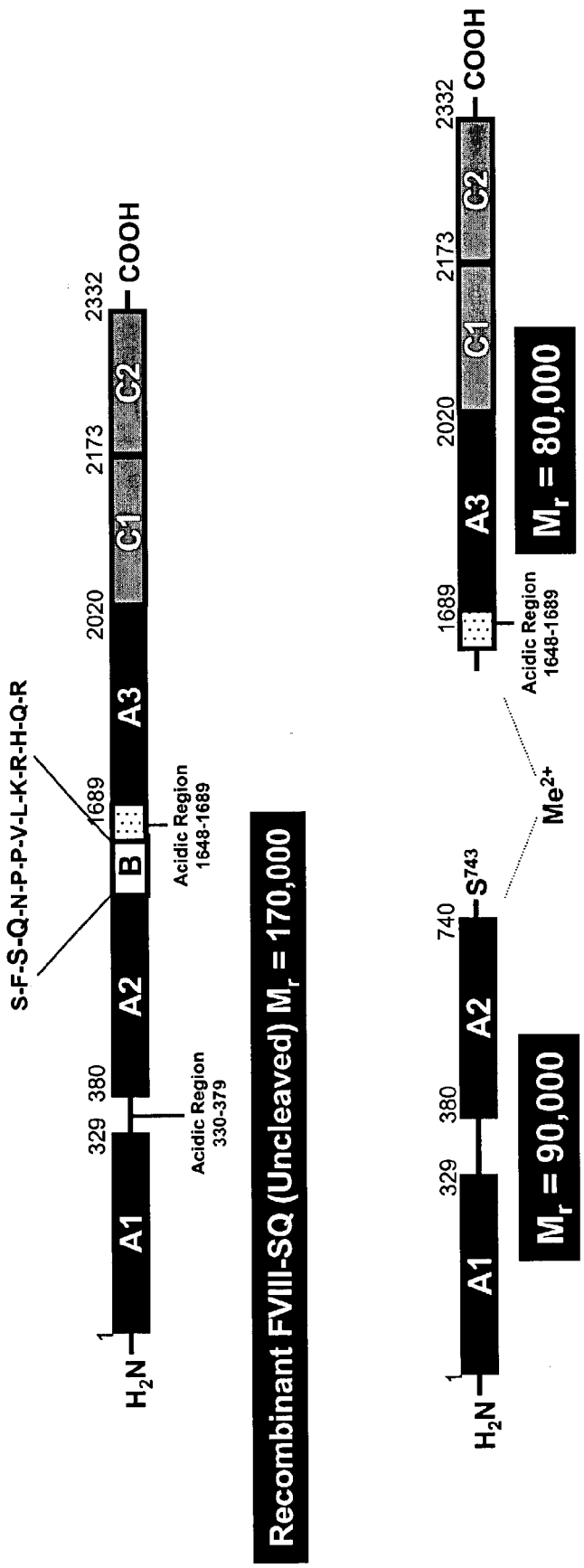
FIG. 2 is a schematic diagram of recombinant Factor VIII-SQ.

The rFVIII-SQ construct, currently in use by several groups, is the shortest version of a FVIII gene currently reported. See FIG. 2. rFVIII-SQ is a deletion derivative of FVIII, lacking the major part of the central B-domain. The N- and C-terminal parts of the B-domain are retained and fused at Ser$^{743}$-Gln$^{1638}$. The molecular mass of rFVIII-SQ is 170 kDa, comprising a 90 kDa heavy chain and a 80 kDa light chain (in the cleaved, secreted form), which are non-covalently associated. rFVIII-SQ has structural and functional properties which are similar to those of plasma-derived FVIII (similar specific activity; theoretical specific activity of purified plasma-derived FVIII is 5000–6000 IU/mg assuming 1U/mL FVIII activity is equal to 1500–200 ng/mL). The product has been developed by Pharmacia AB, Biopharmaceuticals, Stockholm, Sweden and Genetics Institute under the ReFacto Trade name. Information on the product can be found in the following references: Lind, et al., (1995) Eur J. Biochem 232, 19–27; Berntorp, E., (1997) Thrombosis and Haemostasis 78, 256–260; and Sandberg, H., et al. (2001) Seminars in Hematology 38, 4–12. rFVIII-SQ is disclosed in U.S. Pat. No. 5,661,008 issued in Aug. 26, 1997 and assigned to Kabi Pharmacia AB (Upsala, SE).

rFVIII-SQ encodes a Factor VIII molecule which is efficiently processed in mammalian cells. The single chain molecule, following post-translational modification is cleaved at Arg$^{1648}$, by an unknown PACE-furin-like enzyme and FVIII-SQ is secreted in the surrounding milieu as a heterodimer (A1-A2-B(partial)) and (B(partial)-A3-C1-C2), and this molecule is efficiently cleaved by thrombin (at Arg$^{372}$, Arg$^{740}$, and Arg$^{1689}$) to yield biologically active rFVIIIa (heterotrimers; A1, A2, A3-C1-C2).

The present invention differs from the current technology in the following ways: 1) the constructs described herein encode VIII variants that are ~55–~75 amino acids shorter, lacking the so-called acidic region, all of the B-domain, and in some cases part of the C-terminal of the A2 domain; 2) based on our findings the current invention has greater activity (~5–13-fold) compared to rFVIII-SQ in a one-stage APTT clotting assay. See FIGS. 5–7 and Table I.

The invention represents a significant improvement over rFVIII-SQ. First, the constructs are ~150–~200 bp shorter than the cDNA sequence for rFVIII-SQ, thus allowing for more efficient packaging into, for example, AAV vectors, which may allow for the incorporation of enhancer elements or more efficient promoters into any gene delivery construct. Second, since the new constructs appear to have a greater specific activity in a one-stage APTT assay, potentially less protein may be needed to correct a prolonged APTT.

The recombinant constructs are efficiently synthesized as a single chain molecule initially. The PACE-furin-like enzyme should efficiently remove the inserted protease cleavage site in the ER or Golgi. This gives rise to a two-chain or heterodimeric rFVIII which is secreted in the extracellular space. These two chains are held together by divalent metal ions.

Figure 3:
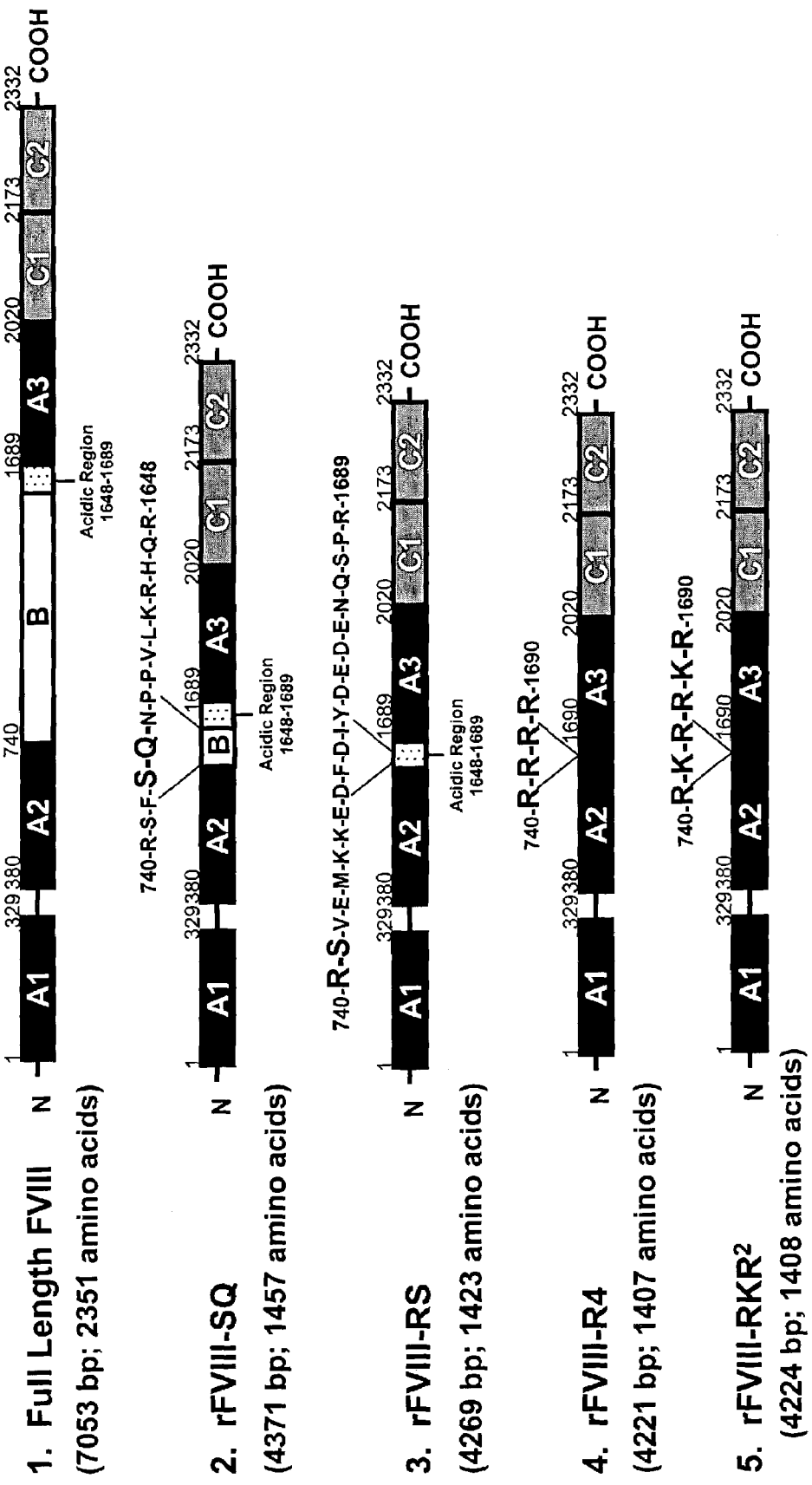
FIG. 3 depicts full length FVIII, rFVIII-SQ, rFVIII-RS, and recombinant FVIII constructs of the present invention, rFVIII-R4 and rFVIII-RKR$^2$. Numbers in parentheses indicate the base pairs of the entire FVIII gene construct and total amino acids, including the signal sequence.
Figure 4:
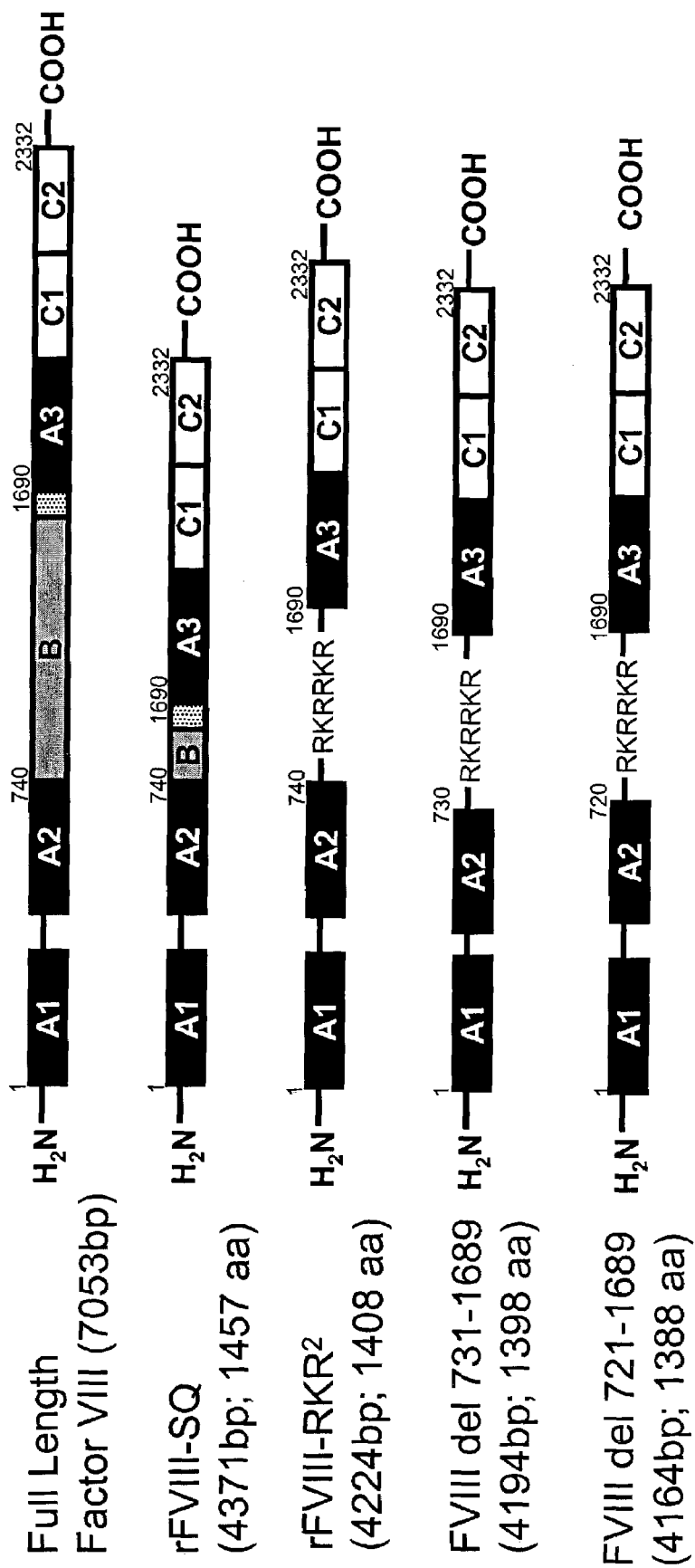
FIG. 4 depicts full length FVIII, rFVIII-SQ, and the recombinant FVIII constructs of the present invention, FVIII (Δ721–1689) and FVIII(Δ731–1689). Numbers in parentheses indicate the base pairs of the entire FVIII gene construct and total amino acids, including the signal sequence.
Figure 5:
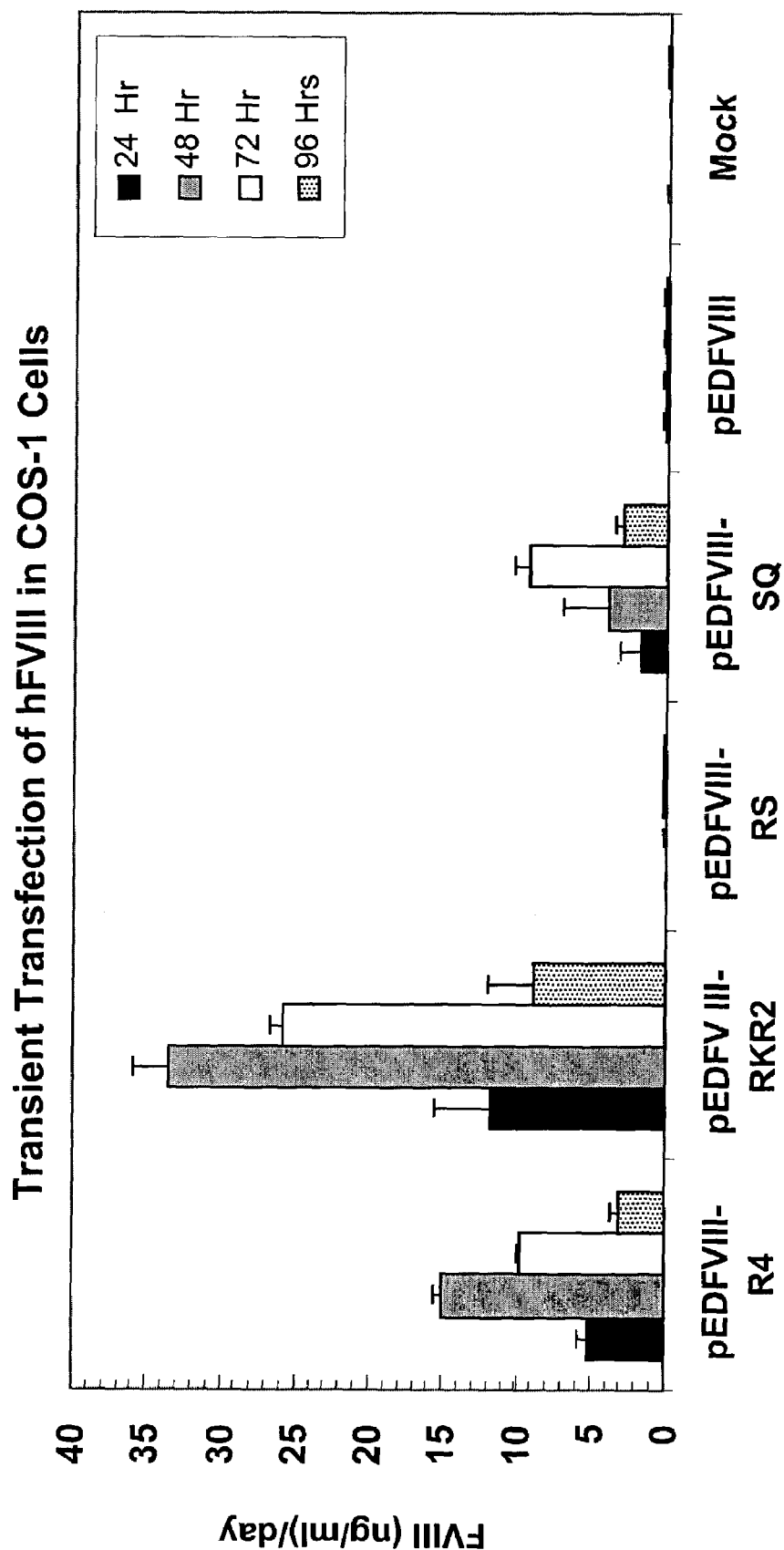
FIG. 5 is a graph showing FVIII levels expressed by the various constructs shown in FIG. 3 in transiently transfected COS-1 cells.
Figure 7:
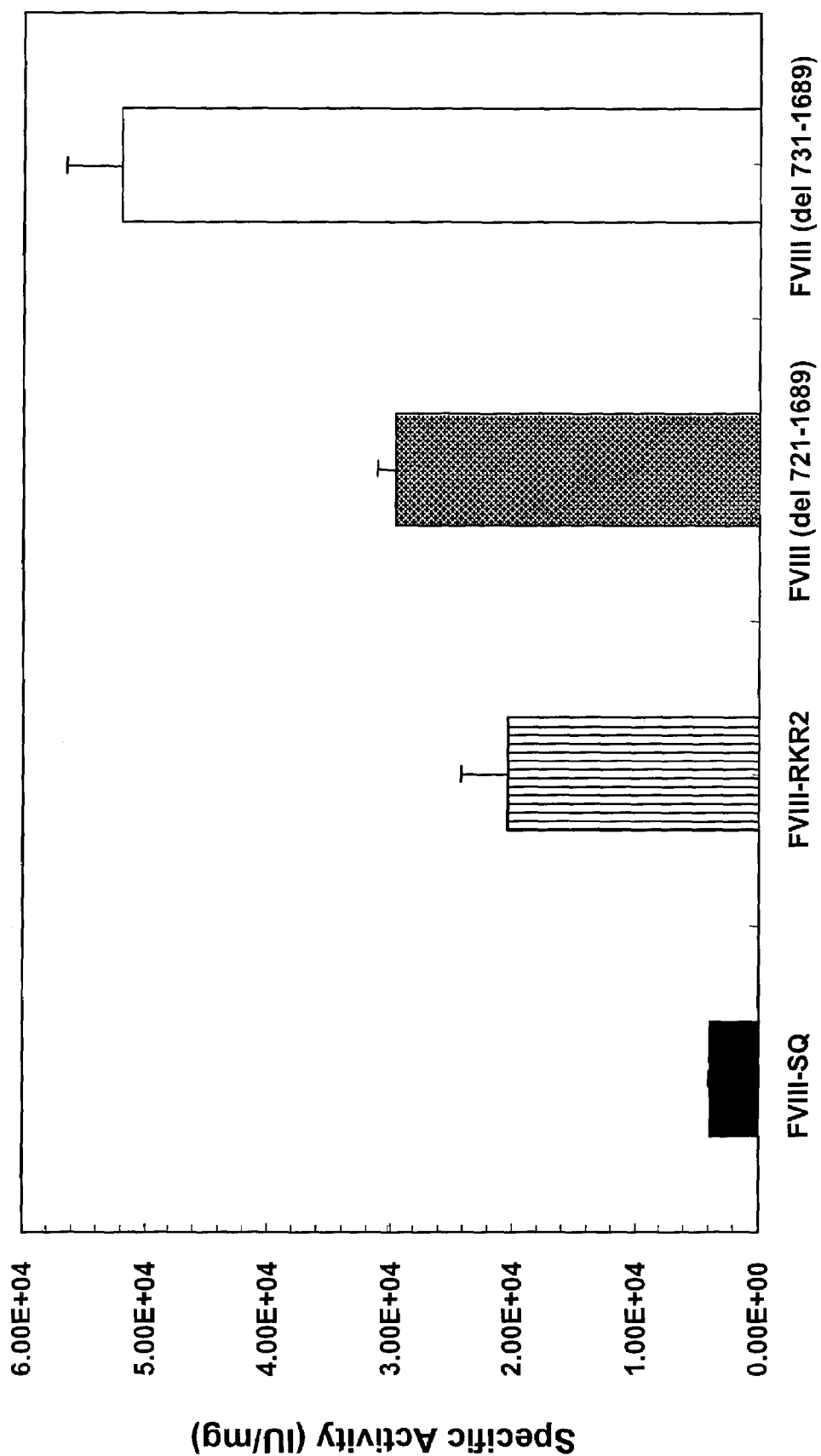
FIG. 7 is a graph showing Factor VIII levels expressed by the various constructs shown in FIG. 4 in transiently transfected COS-1 cells.

We have introduced the modified FVIII constructs shown in FIGS. 3 and 4 into COS-1 cells, BHK cells, and HepG2 cells, and the modified constructs (rFVIII-R4, rFVIII-RKR$^2$, FVIII(Δ721–1689), and FVIII(Δ731–1689)) have enhanced activity compared to full length FVIII and rFVIII-SQ (FIGS. 5–7 and Table I). This may result from either 1) enhanced secretion; 2) partial cofactor activity upon secretion; or 3) enhanced processing by thrombin or other protease (since two out of the three thrombin cleavage sites have been eliminated or are essentially already processed). These novel rFVIII constructs only need to be cleaved by thrombin at Arg372 to become fully processed to FVIIIa; in contrast full length FVIII and FVIII-SQ need to be processed at 372, 740, and 1689 to yield the active cofactor FVIIIa.

Transient transfection data of rFVIII-SQ, rFVIII-R4, and rFVIII-RKR$^2$ are shown in FIG. 5. Results are based on a one-stage FVIII-specific APTT clotting assay and values are expressed as ng/mL FVIII/day for each construct, where 150 ng/mL is equal to 1 IU/mL FVIII activity.

Stable cell lines were also made in BHK cells for rFVIII-SQ and rFVIII-RKR$^2$. In this experiment, each of the FVIII constructs were introduced into BHK cells using a Neomycin gene as a selectable marker. Each stable cell line was placed in a T25 flask and when cells reached 95% confluency, the media was changed and FVIII activity and antigen levels were measured 24 hr later. Specific activities were calculated based on a one-stage APTT clotting assay and a FVIII-specific ELISA using ReFacto as a standard in both assays (FIG. 6). Based on these data, rFVIII-RKR$^2$ has ~7–8-fold increase in specific activity (IU/mg) based on a one-stage FVIII specific APTT clotting assay.

FIG. 7 shows the transient transfection data for rFVIII-SQ, rFVIII-RKR$^2$, FVIII(Δ721–1689), and FVIII (Δ731–1689). Cos-1 cells (100 mm plates) were transiently transfected with various FVIII constructs (25 μg) using Lipofectamine-2000. At selected time points, media from each well was removed and FVIII activity was assessed by a one-stage FVIII-specific APTT using FVIII-deficient plasma. FVIII antigen levels were determined by FVIII specific ELISA. The data are expressed as specific activity, where 1 unit of FVIII activity is equal to 200 ng/mL. The cells were cultured in OPTIMEN supplemented with insulin-transferrin-selenite, CaCl$_2$, and Albumax. Table I is a summary of the results from FIG. 7.

TABLE I

Summary of Results from FIG. 7

| | ELISA (ng/ml) | Clotting Assay (IU/mg) | Specific Act. (IU/mg) | SD |
|---|---|---|---|---|
| FVIII-SQ | 68.70 | 0.27 | 3938.19 | 100.27 |
| FVIII-RKR2 | 6.50 | 0.13 | 20380.22 | 3903.9 |
| FVIII (721-1789) | 12.95 | 0.41 | 29614.63 | 1442.6 |
| FVIII (731-1689) | 7.08 | 0.37 | 1861.87 | 4551.6 |

Additional exemplary constructs of the invention include those set forth are described in Table II:

TABLE II

Variant FVIII Polypeptides

Heavy Chain and B-domain Deletions:

1-740 *(Δ 741–1689) 1690–2332
1-730 *(Δ 731–1689) 1690–2332
1-720 *(Δ 721–1689) 1690–2332
1-710 *(Δ 711–1689) 1690–2332
1-700 *(Δ 701–1689) 1690–2332

B-domain and Light Chain Deletions:

1-740 *(Δ 741–1699) 1700–2332
1-740 *(Δ 741–1709) 1710–2332
1-740 *(Δ 741–1719) 1720–2332
1-740 *(Δ 741–1729) 1730–2332

Heavy and Light Chain Deletions:

1-730 *(Δ 731–1699) 1700–2332
1-730 *(Δ 731–1709) 1710–2332
1-730 *(Δ 731–1719) 1720–2332
1-730 *(Δ 731–1729) 1730–2332
1-720 *(Δ 721–1699) 1700–2332
1-720 *(Δ 721–1709) 1710–2332
1-720 *(Δ 721–1719) 1720–2332
1-720 *(Δ 721–1729) 1730–2332
1-710 *(Δ 711–1699) 1700–2332
1-710 *(Δ 711–1709) 1710–2332
1-710 *(Δ 711–1719) 1720–2332
1-710 *(Δ 711–1729) 1730–2332
1-700 *(Δ 701–1699) 1700–2332
1-700 *(Δ 701–1709) 1710–2332
1-700 *(Δ 701–1719) 1720–2332
1-700 *(Δ 701–1729) 1730–2332

*Note in all constructs, the amino acid numbers are correspond to SEQ ID NO: 2. Between the asterisk indicates the presence of at least one PACE-furin or PACE furin-like cleavage site. Exemplary PACE-furin or PACE turin-like cleavage sites include, but are not limited to, RRRR (SEQ ID NO: 4) or RKRRKR (SEQ ID NO: 5).

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. An isolated nucleic acid sequence which encodes a biologically active recombinant human factor VIII (FVIII) variant, wherein said FVIII variant comprises two segments connected by at least one PACE-furin cleavage site, wherein said segments are selected from the group consisting of:

a) a first segment consisting of the sequence of amino acids 1 to 700 of SEQ ID NO: 2 and a second segment consisting of the sequence of amino acids 1690 to 2332 of SEQ ID NO: 2;

b) a first segment consisting of the sequence of amino acids 1 to 710 of SEQ ID NO: 2 and a second segment consisting of the sequence of amino acids 1690 to 2332 of SEQ ID NO: 2;

c) a first segment consisting of the sequence of amino acids 1 to 720 of SEQ ID NO: 2 and a second segment consisting of the sequence of amino acids 1690 to 2332 of SEQ ID NO: 2;

d) a first segment consisting of the sequence of amino acids 1 to 730 of SEQ ID NO: 2 and a second segment consisting of the sequence of amino acids 1690 to 2332 of SEQ ID NO: 2;

e) a first segment consisting of the sequence of amino acids 1 to 740 of SEQ ID NO: 2 and a second segment consisting of the sequence of amino acids 1700 to 2332 of SEQ ID NO: 2;

f) a first segment consisting of the sequence of amino acids 1 to 740 of SEQ ID NO: 2 and a second segment consisting of the sequence of amino acids 1710 to 2332 of SEQ ID NO: 2;

g) a first segment consisting of the sequence of amino acids 1 to 740 of SEQ ID NO: 2 and a second segment consisting of the sequence of amino acids 1720 to 2332 of SEQ ID NO: 2;

h) a first segment consisting of the sequence of amino acids 1 to 740 of SEQ ID NO: 2 and a second segment consisting of the sequence of amino acids 1730 to 2332 of SEQ ID NO: 2;

i) a first segment consisting of the sequence of amino acids 1 to 730 of SEQ ID NO: 2 and a second segment consisting of the sequence of amino acids 1700 to 2332 of SEQ ID NO: 2;

j) a first segment consisting of the sequence of amino acids 1 to 730 of SEQ ID NO: 2 and a second segment consisting of the sequence of amino acids 1710 to 2332 of SEQ ID NO: 2;

k) a first segment consisting of the sequence of amino acids 1 to 730 of SEQ ID NO: 2 and a second segment consisting of the sequence of amino acids 1720 to 2332 of SEQ ID NO: 2;

l) a first segment consisting of the sequence of amino acids 1 to 730 of SEQ ID NO: 2 and a second segment consisting of the sequence of amino acids 1730 to 2332 of SEQ ID NO: 2;

m) a first segment consisting of the sequence of amino acids 1 to 720 of SEQ ID NO: 2 and a second segment consisting of the sequence of amino acids 1700 to 2332 of SEQ ID NO: 2;

n) a first segment consisting of the sequence of amino acids 1 to 720 of SEQ ID NO: 2 and a second segment consisting of the sequence of amino acids 1710 to 2332 of SEQ ID NO: 2;

o) a first segment consisting of the sequence of amino acids 1 to 720 of SEQ ID NO: 2 and a second segment consisting of the sequence of amino acids 1720 to 2332 of SEQ ID NO: 2;

p) a first segment consisting of the sequence of amino acids 1 to720 of SEQ ID NO: 2 and a second segment consisting of the sequence of amino acids 1730 to 2332 of SEQ ID NO: 2;

q) a first segment consisting of the sequence of amino acids 1 to 710 of SEQ ID NO: 2 and a second segment consisting of the sequence of amino acids 1700 to 2332 of SEQ ID NO: 2;

r) a first segment consisting of the sequence of amino acids 1 to 710 of SEQ ID NO: 2 and a second segment consisting of the sequence of amino acids 1710 to 2332 of SEQ ID NO: 2;

s) a first segment consisting of the sequence of amino acids 1 to 710 of SEQ ID NO: 2 and a second segment consisting of the sequence of amino acids 1720 to 2332 of SEQ ID NO: 2;

t) a first segment consisting of the sequence of amino acids 1 to 710 of SEQ ID NO: 2 and a second segment consisting of the sequence of amino acids 1730 to 2332 of SEQ ID NO: 2;

u) a first segment consisting of the sequence of amino acids 1 to 700 of SEQ ID NO: 2 and a second segment consisting of the sequence of amino acids 1700 to 2332 of SEQ ID NO: 2;

v) a first segment consisting of the sequence of amino acids 1 to 700 of SEQ ID NO: 2 and a second segment consisting of the sequence of amino acids 1710 to 2332 of SEQ ID NO: 2;

w) a first segment consisting of the sequence of amino acids 1 to 700 of SEQ ID NO: 2 and a second segment consisting of the sequence of amino acids 1720 to 2332 of SEQ ID NO: 2; and x) a first segment consisting of the sequence of amino acids 1 to 700 of SEQ ID NO: 2 and a second segment consisting of the sequence of amino acids 1730 to 2332 of SEQ ID NO: 2;

wherein said FVIII variant lacks amino acids 1648 to 1689 of SEQ ID NO: 2 ; and wherein said variant has FVIII activity.

2. The nucleic acid sequence of claim 1, wherein said PACE-furin cleavage site is selected from the group consisting of RRRR (SEQ ID NO: 4) and RKRRKR (SEQ ID NO: 5).

3. The nucleic acid sequence of claim 1, wherein the first segment consists of the sequence of amino acids 1 to 730 of SEQ ID NO: 2 and the second segment consists of the sequence of amino acids 1690 to 2332 of SEQ ID NO: 2.

4. The nucleic acid sequence of claim 1, wherein the first segment consists of the sequence of amino acids 1 to 720 of SEQ ID NO: 2 and the second segment consists of the sequence of amino acids 1690 to 2332 of SEQ ID NO: 2.

5. The nucleic acid sequence of claim 1 further comprising 5' and 3' regulatory signals for expression of said nucleic acid sequence in transformed cells.

6. A vector comprising the nucleic acid sequence of claim 1.

7. An isolated modified human FVIII protein produced by expression of the nucleic acid of claim 1.

8. A method of treating hemophilia in a patient in need thereof, comprising:
a) providing a variant FVIII polypeptide produced by the expression of the nucleic acid sequence of claim 1 in a biologically acceptable carrier; and
b) administering an effective amount of said polypeptide to said patient under conditions that result in a beneficial therapeutic effect in said patient.

9. The method of claim 8, wherein said biologically acceptable carrier further comprises a liposome.

* * * * *